United States Patent
Fischer et al.

(10) Patent No.: US 9,802,985 B2
(45) Date of Patent: Oct. 31, 2017

(54) PHARMACEUTICAL COMPOSITION FOR TREATMENT OF THE PULMONARY FORM OF ALTITUDE SICKNESS CAUSED BY LACK OF OXYGEN AND REDUCED AIR PRESSURE

(71) Applicant: APEPTICO FORSCHUNG UND ENTWICKLUNG GMBH, Vienna (AT)

(72) Inventors: Bernhard Fischer, Vienna (AT); Rudolf Lucas, Martinez, GA (US); Hendrik Fischer, Vienna (AT)

(73) Assignee: APEPTICO FORSCHUNG UND ENTWICKLUNG GMBH, Vienna (AT)

( * ) Notice: Subject to any disclaimer, the term of this patent is extended or adjusted under 35 U.S.C. 154(b) by 0 days.

(21) Appl. No.: 14/410,642

(22) PCT Filed: Jun. 19, 2013

(86) PCT No.: PCT/EP2013/062777
§ 371 (c)(1),
(2) Date: Dec. 23, 2014

(87) PCT Pub. No.: WO2014/001177
PCT Pub. Date: Jan. 3, 2014

(65) Prior Publication Data
US 2015/0225460 A1    Aug. 13, 2015

(30) Foreign Application Priority Data
Jun. 28, 2012   (EP) .................................. 12173983

(51) Int. Cl.
| A61K 38/12 | (2006.01) |
| C07K 7/64  | (2006.01) |
| A61P 11/00 | (2006.01) |
| A61K 38/19 | (2006.01) |

(52) U.S. Cl.
CPC .............. *C07K 7/64* (2013.01); *A61K 38/191* (2013.01)

(58) Field of Classification Search
CPC ................................ A61K 38/191; C07K 7/64
See application file for complete search history.

(56) References Cited

U.S. PATENT DOCUMENTS

2011/0319316 A1* 12/2011 Fischer ................. A61K 38/12
                                                             514/1.5

FOREIGN PATENT DOCUMENTS

| EP | 2009023 A1    | 12/2008 |
| WO | 0009149       | 2/2000  |
| WO | 2006013183 A1 | 2/2006  |
| WO | 2009073909 A1 | 6/2009  |
| WO | 2010099556 A1 | 9/2010  |
| WO | 2011085423 A1 | 7/2011  |
| WO | 2012065201 A1 | 5/2012  |

OTHER PUBLICATIONS

Rudinger, Peptide Hormones, JA Parsons, Ed., 1976, pp. 1-7.*
SIGMA, 2004, pp. 1-2.*
Berendsen, A Glimpse of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Mac Sweeney et al, Nasal potential difference to detect Na+ channel dysfunction in acute lung injury, Am J Physiol Lung Cell Mol Physiol, 2011, 300, pp. L305-L318.*
Machine translation of WO 2011/085423 A1, pp. 1-25, accessed Jan. 18, 2016.*
Machine translation of WO 2012/065201 A1, pp. 1-18, accessed Jan. 18, 2016.*
Maggiorini, Prevention and Treatment of High-Altitude Pulmonary Edema, Progress in Cardiovascular Diseases, 2010, 52, pp. 500-506.*
Fiore et al, Altitude Illness: Risk Factors, Prevention, Presentation, and Treatment, Am Fam Physician, 2010, 82, pp. 1103-1110.*
Developing Products for Rare Diseases & Conditions, from http://www.fda.gov/forindustry/developingproductsforrarediseasesconditions/default.htm, pp. 1-3, accessed Jul. 6, 2016.*
Definition of Prophylactic, from http://www.merriam-webster.com/dictionary/prophylactic, pp. 1-3, accessed Jul. 5, 2016.*
Drugs used to Prevent & Treat Mountain Sickness, from http://web.archive.org/web/20051125225410/http://www.traveldoctor.co.uk/diamox.htm, Nov. 25, 2005, pp. 1-4.*
Why do clinical trials fail?, from http://www.clinicaltrialsarena.com/news/operations/why-do-clinical-trials-fail-4669215, Sep. 11, 2015, pp. 1-3.*
Fagenholz et al, Treatment of high altitude pulmonary edema at 4240 m in Nepal, High Alt Med Biol., Aug. 2007, pp. 139-146.*
Eaton, Douglas et al., "Ion transport across epithelial tissues: new insight from single-channel measurements," Symposium (1986) p. 2707.
Hamill, O.P. et al., "Improved Patch-Clamp Techniques for High-Resolution Current Recording from Cells and Cell-Free Membrane Patches," Pflugers Arch (1981) 391, pp. 85-100.

(Continued)

*Primary Examiner* — Julie Ha
*Assistant Examiner* — Li Ni Komatsu
(74) *Attorney, Agent, or Firm* — Edwin S. Flores; Daniel J. Chalker; Chalker Flores, LLP

(57) ABSTRACT

What is described is a peptide which consists of 7-20, especially 7-17, adjacent amino acids and comprises the hexamer $TX_1EX_2X_3E$ where $X_1$, $X_2$ and $X_3$ may be any natural or unnatural amino acid, where the peptide does not have any TNF receptor binding activity and is cyclized, for use for the treatment and avoidance of the pulmonary form of altitude sickness.

10 Claims, 7 Drawing Sheets

(56) References Cited

OTHER PUBLICATIONS

Hazemi, Parastoo et al., "Essential Structural Features of TNA—a Lectin-like Domain Derived Peptides for Activation of Amiloride-Sensitive Sodium Current in A549 Cells," J. Med. Chem. (2010) 53, pp. 8021-8029.
Hollenhorst, Monika I. et al., "Ion Transport by Pulmonary Epithelia," J. Biomedicine and Biotechnology (2011) 16 pages.
Hribar, Marusa et all., "The lectin-like domain of tumor necrosis factor-a increases membrane conductance in microvascular endothelial cells and peritoneal macrophages," Eur. J. Immunol. (1999) 29, pp. 3105-3111.
Lazrak, A. et al., "Biophysical properties and molecular characterization of amiloride-sensitive sodium channels in A549 cells," Am J Physiol Lung Xcell Mol Physial (2000) 278, pp. L848-L857.
Maggiorini, Marco, "High altitude-induced pulmonary oedema," Cardiovascular Research (2006) 72, pp. 41-50.
Tzotzos, Susan et al., "AP301, a synthetic peptide mimicking the lectin-like domain of TNF, enhances amiloride-sensitive Na+ current in primary dog, pig and rat alveolar type II cells," Pulmonary Pharmacology & Therapeutics (2013) pp. 1-8.
Zhou Q, et al. "Solnatide demonstrates profound therapeutic activity in a rat model of pulmonary edema induced by acute hypobaric hypoxia and exercise", Chest (2016), doi: 10.1016/j.chest.2016.10.030.
Maggiorini, Marco, "High altitude-induced pulmonary oedema" Cardiovascular Research 72 (Jun. 2006) 41-50.
Sweeney, R. Mac et al., "Nasal potential difference to detect Na+ channel dysfunction in acute leg injury" Am J. Physiol Lung Cell Physiol 300 L305-L318 Jul. 2010.

\* cited by examiner

PHARMACEUTICAL COMPOSITION FOR TREATMENT OF THE PULMONARY FORM OF ALTITUDE SICKNESS CAUSED BY LACK OF OXYGEN AND REDUCED AIR PRESSURE

CROSS-REFERENCE TO RELATED APPLICATIONS

This application is a national stage application under 35 U.S.C. 371 of PCT/EP2013/062777 filed on Jun. 19, 2013 and claims foreign priority to European Patent Office (EPO) Application No. 12173983.3 filed on Jun. 28, 2012.

TECHNICAL FIELD OF THE INVENTION

The present invention relates to the treatment of the pulmonary form of altitude sickness caused by lack of oxygen and reduced air pressure.

STATEMENT OF FEDERALLY FUNDED RESEARCH

None.

REFERENCE TO A SEQUENCE LISTING

The present application includes a Sequence Listing which has been submitted in ASCII format and is hereby incorporated by reference in its entirety. The ASCII copy was created on Dec. 23, 2014 and is named SEQUENCE-LISTINGascii.txt and is 6 KB in size.

BACKGROUND OF THE INVENTION

Altitude sickness can occur in humans from a height of over 2500 m above sea level. At a height of over 2500 meters, the oxygen concentration and the air pressure decrease considerably. A differentiation is made between cerebral and pulmonary forms of acute altitude sickness. Acute altitude sickness therefore occurs in the brain and also in the lung. The first detailed clinical description of altitude sickness took place during a Mont Blanc expedition in 1891. At least four members of the expedition suffered from altitude sickness, with one member dying on 2 Sep. 1891 at a height of 4000 m. Since these cases, altitude sickness is deemed to be an individual life-threatening clinical condition.

If untreated, the pulmonary form of altitude sickness can lead to death in less than 24 hours, with death frequently occurring through a secondary pulmonary embolism.

The most effective treatment of all forms of acute altitude sickness is the supply of oxygen, for example by rapid descent of the sufferer to lower altitudes, or by means of bottled oxygen or by means of a portable hyperbaric chamber. However, in mountainous regions, a rapid descent is often not possible. Oxygen ventilation by e.g. bottled oxygen does indeed reduce the increased pulmonary arterial pressure, but does not normalize it. Also, in the case of a portable hyperbaric chamber, the positive effect is only temporary. The success of the therapy disappears in patients immediately after leaving the hyperbaric chamber, when they become physically active again.

A medicinal treatment for altitude sickness is currently only limited and controversial: Thus, dexamethasone is suggested in severe acute altitude sickness and also specifically in the cerebral form of altitude sickness. Furthermore, it has been discussed whether PDE-5 inhibitors, which are used for the treatment of primary pulmonary arterial hypertension (Dana Point Classification 1) are also indicated for secondary pulmonary hypertension through lack of oxygen at altitudes (Dana Point Classification 3).

Natural treatment possibilities for altitude sickness (also preventatively) were also proposed (tea from the leaves of the coca bush; yak butter tea; preparations which contain ginkgo as active ingredient).

However, it is to be noted that currently the possibility for medicinal treatment of the pulmonary form of altitude sickness is still very limited. Furthermore, it is known that organized rescue operations can only be counted upon in the European alpine region and partly also in the North American region. In remote high mountains of the world and in extreme altitudes, rescue operations and medical aid in emergencies (with the use of bottled oxygen or portable hyperbaric chamber) are scarcely possible. The provision of an efficient medicinal treatment of altitude sickness would therefore be urgently necessary, also as a component as emergency pack for mountaineers who may be at risk of developing altitude sickness.

In EP 2 009 023 A1 new peptides are proposed for the treatment of oedemas. These peptides are evaluated here by the "TEER" ("Transepithelial electrical resistance") test using Calu-3 cells, which does not constitute an established test system for fluid clearance in pulmonary oedemas (pulmonary oedema fluid clearance). Calu-3 cells are in fact bronchial cells which only constitute approximately 1% of the surface of the lung serving for gas exchange. In contrast, alveolar cells constitute 99% of the surface of the lung serving for gas exchange (Hollenhorst et al., J. Biomed. Biotechnol. 2011 (2011), doi:10.1155/2011/174306). In contrast to the TEER test, the human alveolar epithelial cell line A549 is established as accepted experimental standard as a model for alveolar epithelial cells (Lazrak et al., Am. J. Physiol. Lung Cell. Mol. Physiol. 278 (2000), L848-57).

It is therefore an object of the present invention to distinctly improve the possibilities for the medicinal treatment of patients with the pulmonary form of altitude sickness and to make available a means by which this disease can be effectively treated, but also avoided.

SUMMARY OF THE INVENTION

Accordingly, the present invention concerns a peptide which consists of 7-20, especially 7-17 adjacent amino acids and comprises the hexamer $TX_1EX_2X_3E$, where $X_1$, $X_2$ and $X_3$ may be any natural or unnatural amino acid, where the peptide does not have TNF receptor binding activity and is cyclized, for the treatment and prevention of the pulmonary form of altitude sickness.

With the present invention, for the first time a medicinal therapy was able to be made available for the pulmonary form of altitude sickness. Therefore, an "orphan drug designation" was also granted immediately for the present invention, and namely both by the EMA (EMA/OD/144/12) and also by the US-FDA (12-3829). This shows the urgent need for a possibility of treatment for this disease, which is met by the present invention.

The peptides to be used according to the invention have been already known per se for a long time, for example from the European Patent EP 1 264 599 B1, the US 2007/299003 A, WO 94/18325 A1, WO 00/09149 A1, WO 2006/013183 A1 or WO 2008/148545 A1. In the course of the experiments for the present invention, it was now recognized that these peptides are surprisingly also suitable for treating the pulmonary form of altitude sickness, so that therefore for the first time a simple and efficient medicinal treatment form can be made available for this indication.

These peptides—which are known per se —, which come into use according to the invention do not have TNF receptor binding activity (Hribar et al., Eur. J. Immunol. 1999; Elia et al., AJRCCM 2003; see also: Example section below) and are cyclized. Preferred variants of these peptides consist of 7-17 adjacent amino acids and contain the hexamer TPE-GAE (SEQ ID NO: 2).

Acute altitude sickness always begins with subacute hypoxia. Subsequently, hypoxaemia and hypercapnia lead to vasodilatation, hypocapnia to vasoconstriction. At altitude, different effects now result from hypoxaemia and hypocapnia: In the lung, vasoconstriction predominates, and in the brain vasodilatation.

The cause of acute altitude sickness lies in a failed adaptation, primarily in a ventilation increase which is individually too little (relative hypoventilation). The consequences are a more marked hypoxaemia, higher pulmonary arterial pressure, higher intracranial pressure, fluid retention and lower erythropoiesis.

The pulmonary form of altitude sickness is caused by lack of oxygen and reduced air pressure and is a life-threatening change to lung function and occurs principally at heights of between 2500 and 6000 m. Two thirds of all cases occur between 3000 and 4500 m above sea level. The pulmonary form of altitude sickness is the most frequent cause of death in acute altitude sickness.

The pulmonary form of altitude sickness often begins characteristically after exceeding the threshold height of approximately 2500 m.

The excess, non-homogeneous, hypoxic vasoconstriction in the lung leads to overperfused areas of the lung with acute infiltrates. The greatly increased pulmonary hypertension as a result of a non-homogeneous hypoxic vasoconstriction is an expression, principally in peripheral areas of the lung, of a greatly increased hypoxic pulmonary vascular response (HPVR) in previously fully healthy humans. An increase in the pulmonary arterial pressure is indeed physiological under hypoxia, but is considerably more strongly marked in the pulmonary form of altitude sickness. However, the pulmonary capillary permeability is not increased under hypoxia.

This is in clear contrast to other acute lung diseases, such as for example acute lung injury (ALI), acute respiratory distress syndrome (ARDS) or hyperpermeability oedema, which can occur either in primary form through direct action of a noxa or in secondary form as a consequence of other diseases. The most frequent impairments to the lung in ALI, ARDS and in hyperpermeability oedema are bacterial and viral pneumonia, lung contusion, aspiration of gastric juice, inhalation trauma, smoke toxicopathies, near drowning, massive blood transfusions, sepsis, polytrauma, cardiopulmonary bypass or extensive burns. In these lung diseases, the inflammatory reaction with accompanying damage to the alveolar walls is in the forefront. This condition leads to a complex activation of pro- and anti-inflammatory immune processes, which lead to inflammatory damage to the alveolar epithelium and the vessel endothelium. The consequences are loss of alveolocytes and surfactant, the occurrence of a capillary leak with discharge of plasma proteins and interstitial oedema formation. The inflammatory changes are typically patchy and distributed non-homogeneously over the entire lung. Infiltration, interstitial and alveolar oedema ultimately lead to atelectases and the clinical signs of arterial hypoxaemia and pulmonary hypertension. Such inflammatory reactions have no pathological significance in altitude sickness.

The incidence of a clinically manifest pulmonary form of altitude sickness lies above 3500 m at around 15%, with lethality lying at 44% of untreated patients.

The incidence of altitude sickness does not correlate with the $VO_{2max}$, training state, blood pressure, nutrition, cigarette smoking or age (in contrast to acute lung injury (ALI/ARDS), in which above all cigarette smoking and old age represent considerable risk factors), but certainly partly with the individual hypoxic ventilatory response (HVR) and with the mountain destination or respectively the rate of climb.

The differences between the treatment of the pulmonary form of altitude sickness on the one hand and ALI/ARDS on the other hand was also regarded by the medicines authorities EMA and US-FDA in the authorisation of the present invention as an "orphan indication" expressly as the basis in the examination of these authorisations. This decision results on the one hand already solely from the international diagnosis classification system (ICD) of the World Health Organisation (WHO): The pulmonary form of altitude sickness is classified there under Chapter XIX (Injury, Poisoning and Certain Other Consequences of External Causes), Disease Group T66-T78 (Other and unspecified effects of external causes), Disease Class T70 (Effects of air pressure and water pressure), Sub-category T70.2 (Other and unspecified effects of high altitude), whereas ALI/ARDS is classified in a completely different chapter (Chapter X (Diseases of the Respiratory System), Disease Group J80-J84 (Other respiratory diseases principally affecting the interstitium), Disease Class J80 (Adult respiratory distress syndrome [ARDS])). The clinical field is different (environmental, occupational and sports medicine for the pulmonary form of altitude sickness; anaesthesia and intensive medicine for ALI/ARDS). The aetiology is fundamentally different. The pulmonary form of altitude sickness develops in otherwise healthy persons without underlying or already existing clinical conditions through the rapid, non-acclimatised ascent by healthy mountain hikers to heights over 3000 m or respectively changes to environmental conditions, whereas ALI/ARDS is caused by previous clinical conditions and as a consequence of an underlying pathophysiology (the patient is already suffering from another, definable clinical condition), such as: severe infection or inflammation, which is local or systemic (e.g. in the case of sepsis), aspiration (e.g. by gastric juice), inhalation of hot or poisonous gases, multiple blood transfusions, near drowning, lung contusion, polytrauma, burns, fat embolism, etc.); likewise pathophysiology. In the pulmonary form of altitude sickness, an insufficient ventilatory response and an unusually strong vasoconstriction reaction lead to hypoxia, through which then (also due to (neurogenic) sympathetic overactivity) increased lung pressure, endothelial stress and capillary exit occur; in ALI/ARDS, alveolar damage, exit of protein-rich fluid into the interstitial and alveolar area and extensive release of cytokines and immigration of neutrophils lead to reduced gas exchange in the lung).

Primarily, however, the pulmonary form of altitude sickness and ALI/ARDS also differ in the role which inflammatory processes have in these diseases. Inflammatory processes always precede ALI/ARDS; these inflammatory processes play a major role in the pathophysiology. In contrast, inflammatory processes play as good as no part in the pulmonary form of altitude sickness; they occur, if at all, only as a secondary feature, but not as the cause of the disease. Whereas therefore in ALI/ARDS an increased secretion of pro-inflammatory modulators from the endothelium and neutrophils, inflammatory responses by neutrophil activation and cytokine release, a high content of cytokines and proteins in the bronchoalveolar lavage fluid (BALF), presence of neutrophils and macrophages in the BALF and increased microvascular lung permeability caused by an acute inflammation represent clear signs of inflammation, these are completely absent at least in the initial phase of the pulmonary form of altitude sickness. BALF analyses show, in the pulmonary form of altitude sickness, no increase of leucocytes or pro-inflammatory modulators and no difference in surfactant protein A and Clara cell protein.

Finally, the diagnosis of the pulmonary form of altitude sickness and ALI/ARDS is completely different: The pulmonary form of altitude sickness occurs in healthy, non-acclimatised mountain hikers and develops within two to five days after arrival at high altitude. Here, the pressure the pulmonary arteries is abnormally increased, but the wedge pressure remains normal. In ALI/ARDS, as mentioned, an initiating clinical condition always exists (e.g. sepsis). The wedge pressure is ≤18 mmHg, in addition there is generally no clinical indication for left atrial high pressure (no increased pressure in the pulmonary artery); the $PaO_2/FiO_2$ ratio is ≤300 (ALI) in stable state.

The pulmonary form of altitude sickness and ALI/ARDS are therefore two diseases which are completely different from one another (Peacock, Eur. Respir. J. 8 (1995), 1819-1821).

Preferably, the present invention relates to a peptide which consists of 7-20, especially 7-17, adjacent amino acids and comprises the hexamer TPEGAE (SEQ ID NO: 2), where the peptide does not have TNF respective binding activity and is cyclized, for the treatment of the pulmonary form of altitude sickness.

A particularly preferred embodiment of the present invention relates to a cyclized peptide, consisting of a sequence of consecutive amino acids, selected from the group consisting of

QRETPEGAEAKPWY (SEQ ID NO: 3)

PKDTPEGAELKPWY (SEQ ID NO: 4)

CGQRETPEGAEAKPWYC, (SEQ ID NO: 1)

CGPKDTPEGAELKPWYC, (SEQ ID NO: 5)

CGQKETPEGAEAKPWYC, (SEQ ID NO: 6)

CGQRETPEGAEARPWYC, (SEQ ID NO: 7)

CGQRETPEGAEAKPC, (SEQ ID NO: 8)

CQRETPEGAEAKPWYC, (SEQ ID NO: 9)

CGQRETPEGAEAKFWYC, (SEQ ID NO: 10)

KSPGQRETPEGAEAKPWYE, (SEQ ID NO: 11)

KGQRETPEGAEAKPWYG, (SEQ ID NO: 12)

ornithine-GQRETPEGAEAKPWYG, (SEQ ID NO: 13)

4-aminobutanoic acid-GQRETPEGAEAKPWYD, (SEQ ID NO: 14)

β-alanine-GQRETPEGAEAKPWYE (SEQ ID NO: 15)

and fragments of at least 7 amino acids thereof, which have the hexamer TPEGAE, for use or respectively for the production of a medicament for the treatment of the pulmonary form of altitude sickness.

Preferably, the peptide contains the amino acid sequence CGQRETPEGAEAKPWYC (SEQ ID NO: 1) and is cyclized via the C residues. This particularly preferred peptide therefore has the following amino acid sequence (SEQ ID NO: 1) ($NH_2$)Cys-Gly-Gln-Arg-Glu-Thr-Pro-Glu-Gly-Ala-Glu-Ala-Lys-Pro-Trp-Tyr-Cys(COOH).

The cyclizing of the peptides according to the invention can be achieved here e.g. either via a direct cyclizing over a disulphide bridge between the two C residues at the N and C terminus, or else by the peptide being coupled via both cysteines to a carrier substance. Here, in the peptides according to the invention, the cysteine residues are preferably provided at the beginning and at the end of the molecule. Other functional groups which achieve a cyclizing of the peptide can also be used, e.g. by an acid group with an amine or alcohol leading to an amide- or ester ring closure (here e.g. the amino acids aspartic acid and glutamic acid can be cyclized with serine, threonine, tyrosine, asparagine, glutamine or lysine, preferably intramolecularly). The cyclizing of the peptide takes place preferably by a disulphide bridge between the C residues of the peptide (if present). However, cysteine residues or other functional groups can also be provided on the carrier substance, in particular on a carrier protein, which bind the N terminus or respectively the C terminus of the peptides according to the invention and thus ensure the cyclic nature of the peptides according to the invention.

In this respect, of course also any reference to a peptide "according to the invention" herein is the reference to a cyclized peptide.

The cyclizing via cysteine residues is particularly preferred according to the invention, in particular via cysteine residues which are provided at the beginning and at the end of the peptides according to the invention or are additionally introduced, and/or are coupled via cysteine residues on a carrier, on the N and C terminus of the peptide according to the invention. The intramolecular cyclizing of the peptides according to the invention via the provided or additionally introduced cysteine residues at the N and C terminus is particularly preferred.

Further preferred peptides according to the invention are therefore, for example, CGQKETPEGAEAKPWYC (SEQ ID NO: 6), CGQRETPEGAEARPWYC (SEQ ID NO: 7), CGQRETPEGAEAKPC (SEQ ID NO: 8), CQRETPEGAEAKPWYC (SEQ ID NO: 9) or CGQRETPEGAEAKFWYC (SEQ ID NO: 10).

A further group of preferred peptides according to the invention are cyclic peptides with a sequence $X_1$-GQRETPEGAEAKPWY-$X_2$ (SEQ ID NO: 21), where $X_1$ represents 1 to 4 amino acids, in particular 1 or 3 amino acids, these amino acids are natural or unnatural amino acids, in particular $X_1$ represents the amino acid C, K, ornithine, 4-aminobutyric acid, β-alanine, or the sequence KSP, $X_2$ can be a natural or unnatural amino acid, where $X_2$ is in particular the amino acid C, D, G or E, and where $X_1$ is the N-terminal amino acid and $X_2$ is the C-terminal amino acid (GQRETPEGAEAKPWY corresponds to SEQ ID NO: 18). Particularly preferred examples of this sequence $X_1$-GQRETPEGAEAKPWY-$X_2$ (SEQ ID NO: 21) are the cyclic peptides KSPGQRETPEGAEAKPWYE (SEQ ID NO: 11), KGQRETPEGAEAKPWYG (SEQ ID NO: 12), ornithine-GQRETPEGAEAKPWYG (SEQ ID NO: 13), 4-aminobutanoic acid-GQRETPEGAEAKPWYD (SEQ ID NO: 14), β-alanine-GQRETPEGAEAKPWYE (SEQ ID NO: 15).

In the cyclic peptide KSPGQRETPEGAEAKPWYE (SEQ ID NO: 11) the amino acids are linked peptidically from the C-terminal amino acid glutamic acid (E) to the N-terminal amino acid lysine (K), whilst the N-terminal amino acid lysine (K) is connected with the C-terminal amino acid glutamic acid (E) by means of an amide bond between the nitrogen of the epsilon amino group of the side chain of the lysine and the gamma carbon in the side group of the glutamic acid.

In the cyclic peptide KGQRETPEGAEAKPWYG (SEQ ID NO: 12) the amino acids are linked peptidically from the C-terminal amino acid glycine (G) to the N-terminal amino acid lysine (K), whilst the N-terminal amino acid lysine (K) is connected with the C-terminal amino acid glycine (G) by means of an amide bond between the nitrogen of the epsilon amino group of the side chain of the lysine and the carbon of the carboxyl group of the glycine.

In the cyclic peptide ornithine-GQRETPEGAEAKPWYG (SEQ ID NO: 13) the amino acids are linked peptidically from the C-terminal amino acid glycine (G) to the N-terminal amino acid ornithine (Orn), whilst the N-terminal amino acid ornithine (Orn) is connected with the C-terminal amino acid glycine (G) by means of an amide bond between the nitrogen of the delta amino group of the side chain of the ornithine and the carbon of the carboxyl group of the glycine.

In the cyclic peptide 4-aminobutanoic acid-GQRETPEGAEAKPWYD (SEQ ID NO: 14) the amino acids are linked peptidically from the C-terminal aspartic acid (D) to the N-terminal amino acid glycine (G), whilst the C-terminal aspartic acid (D) is connected with the N-terminal amino acid glycine by means of an amide bond between the nitrogen of the amino group of the N-terminal glycine and the carbon C1 of the carboxyl group of the 4-aminobutyric acid on the one hand, and by means of an amide bond between the nitrogen of the amino group of the 4-aminobutyric acid and the carbon of the carboxyl group of the side chain of the C-terminal aspartic acid on the other hand.

In the cyclic peptide β-alanine-GQRETPEGAEAKPWYE (SEQ ID NO: 15) the amino acids are linked peptidically from the C-terminal glutamic acid (E) to the N-terminal amino acid glycine (G), whilst the C-terminal glutamic acid (E) is connected with the N-terminal amino acid glycine by means of an amide bond between the nitrogen of the amino group of the N-terminal glycine and the carbon C1 of the carboxyl group of the β-alanine on the one hand, and by means of an amide bond between the nitrogen of the amino group of the β-alanine and the carbon of the carboxyl group of the side chain of the C-terminal glutamic acid on the other hand.

The cyclizing in the peptides according to the invention can take place as mentioned, but also by binding of the peptide to carrier substances. Coming into consideration as such cyclization carrier substances are all established substances able to be used pharmaceutically, which are able e.g. to enter into a covalent bond with the SH groups of the cysteines (or with other naturally present or artificially introduced chemically reactive groups of the peptide), wherein established carrier proteins, such as keyhole limpet hemocyanin (KLH), tetanus toxin etc., are particularly suitable. Also, adjacent bifunctional residues can be provided on the carrier (e.g. acid group adjacent to amine- or alcohol group). In this context, it is important that "cyclizing" includes both the intramolecular ring closure and also the binding in of a carrier (from which the bonded peptide projects (by the N and C terminus of the peptide being bonded to the carrier), wherein the peptide which is cyclized in such a manner shows the cyclic spatial structure and is stabilized accordingly.

A group of particularly preferred peptides according to the invention is therefore the group with the SEQ ID NOS: 1 and 5 to 15).

The peptides according to the invention have in particular an activating effect on the amiloride-sensitive epithelial sodium ion channel (ENaC). This characteristic can be tested advantageously with the methodology according to Eaton et al., (Fed. Proc. 45 (1986), 2707) and Hamill et al. (Pflugers Arch. 391 (1981), 85-100), as presented in the Example Section.

Preferably, the peptide according to the invention is made available for the treatment of the pulmonary form of altitude sickness in a pharmaceutical composition which comprises a pharmaceutically acceptable carrier. The pharmaceutical composition is preferably prepared here in a form which is suitable for being administered to humans.

The term "a pharmaceutical composition" refers to any composition which comprises a peptide, as defined above (naturally also suitable (i.e. not interfering negatively with one another) mixtures of the peptide according to the invention with further active ingredients; however, it is preferred to provide the peptide according to the invention as sole active ingredient, which impedes, improves or heals the conditions described herein. In particular, the term "a pharmaceutical composition" refers to a composition which has a peptide, as described above, and a pharmaceutically acceptable carrier or excipient (both terms can be used interchangeably). Suitable examples of carriers or excipients which are known to the specialist in the art are water, saline solution, sodium phosphate, sodium acetate, sodium carbonate, citrate, glycine, glycylglycine, histidine, lysine, arginine, TRIS and sodium citrate or mixtures thereof. Of course, Ringer's solution, dextrose solution or solutions of non-reducible sugars can also be used; accordingly, mannite, trehalose, saccharose, sorbite, fructose, maltose, lactose or dextran, Hank's solution, fixed oils, ethyl oleate, 5% dextrose in saline solution, substances which improve the isotony and the chemical stability, buffers and preservatives are also suitable as such carriers. Other suitable carriers include any carrier which does not itself induce the production of antibodies which are harmful for the individual receiving the composition, such as proteins, polysaccharides, polylactic acids, polyglycolic acids, polymeric amino acids and amino acid copolymers. In the formulation of the pharmaceutical composition according to the invention, of course the appropriate guidelines (e.g. the (European or US) Pharmacopoeia) are to be followed. Here, the peptide provided in the composition according to the invention, as mentioned, can also be cyclized by direct covalent binding to these carriers.

The pharmaceutical composition according to the invention can be administered (as a medicament) by any suitable method within the knowledge of the specialist in the art, in particular it is preferred to administer the peptide which is to be used according to the invention, or respectively the composition according to the invention, into the lung. The preferred route of administration is inhalation (through aerosols), but also intravenous administration, instillation, oral administration or combinations thereof. In the case of inhalative, parenteral or oral administration, the medicament of this invention is formulated in dose unit form, such as a solution, suspension or emulsion, in combination with the pharmaceutically acceptable excipient defined above. The dosing and manner of administration can, however, also of course depend in particular cases on the respective individual.

Here, the respectively necessary effective quantity is administered to the individual who requires the administration. The "effective quantity" here is to be understood as a quantity which is sufficiently effective in order to achieve the intended therapeutic or prophylactic effect, i.e. e.g. to prevent a further deterioration of the disease or to treat it effectively. Generally here one proceeds from an average patient, but the actual effective quantities of the components in the composition can be formulated so that the type of administration and the age, weight, condition of the patient and extent and progress of the disease are taken into consideration (e.g. by means of a suitable conventional pharmacological protocol).

Preferably, therefore, the pharmaceutically acceptable carrier in the composition according to the invention is selected from water (particularly preferably: water for injection), common salt, sodium phosphate, sodium acetate, sodium carbonate, citrate, glycine, glycylglycine, histidine, lysine, arginine, TRIS, sodium citrate, Ringer's solution, dextrose, mannite, trehalose, saccharose, sorbite, fructose, maltose, lactose or dextran, Hank's solution, fixed oils, ethyl oleate, substances which improve the isotony and the chemical stability, preservatives, pharmaceutically acceptable proteins, polysaccharides, polylactic acids, polyglycolic acids, polymeric amino acids and amino acid copolymers.

The medicament according to the invention can be administered for example so that the peptide of the present invention is given in a dose of between 1 µg/kg and 10 mg/kg, more preferably between 10 µg/kg and 5 mg/kg, most preferably between 0.1 and 2 mg/kg. Preferably, it is given as a bolus dose. However, a continuous inhalation or infusion or an administration by means of repeated administrations can also be used.

Particularly preferred compositions according to the invention contain the peptide in a quantity of 1 µg to 10 g, preferably of 10 µg to 1 g, in particular of 1 mg to 100 mg.

Particularly preferred compositions according to the invention in liquid form contain the peptide in a quantity of 1 µg to 10 g, preferably of 10 µg to 1 g, in particular of 1 mg to 100 mg, and are present in a volume of 0.5 to 10 ml, in particular in a volume of 1 to 5 ml.

The composition according to the invention can preferably also be administered in dry form by means of a powder inhaler. Examples of such powder inhalers which can be used for the present invention are described in the U.S. Pat. Nos. 4,995,385 and 4,069,819; already established products are SPINHALER®, ROTAHALER®, FLOWCAPS®, INHALATOR®, DISKHALER® and AEROLIZER®.

The composition according to the invention can preferably also be administered as an aerosol by means of a liquid nebulizer. Examples of such liquid nebulizers are established products such as Aeroneb® and Pani®.

According to a preferred embodiment, the composition according to the invention is characterized in that the peptide is present in a nebulizable powder formulation or in a nebulizable liquid formulation.

The invention is explained in further detail by means of the following examples and the figures of the drawings, to which, however, it is of course not restricted.

DESCRIPTION OF THE DRAWINGS

Reference is now made to the accompanying figures and in which.

EXAMPLE 1

Use of the peptide with SEQ NO: 1 according to the invention for the treatment of the pulmonary form of altitude sickness.

With the present example, in an experimental rat model of altitude sickness it is shown that the aim according to the invention was achieved by the synthetic peptide according to the invention (SEQ ID NO: 1) being administered to rats suffering from the pulmonary form of altitude sickness. Physical exertion under conditions of reduced oxygen and air pressure, such as occur at high altitudes, are the 2 main factors which lead to the development of the pulmonary form of altitude sickness. Therefore, the selected rat model, in which the rats carried out physical activity under conditions of reduced oxygen and reduced air pressure, simulates a physically strenuous ascent to high altitudes. This takes place without carrying out a prior acclimatization. This corresponds to the scenario such as is to be found in the case of mountaineers who suffer from the pulmonary form of altitude sickness at high altitudes. In the model which was used, the rats develop the typical symptoms for the pulmonary form of altitude sickness, as is to be read in the "intensity of the pulmonary form of altitude sickness", the increased protein concentration in the lung fluid and the histological appearance of the lung tissue. It is further to be noted that the lung damage in this model is not caused by administration of endotoxins, microbes or other agents which are damaging to the lung. An intensified inflammation of the lung does not occur. Also, no specific strain of rat was used for this experiment. Therefore, this rat model is well suited to investigate a medicament for the treatment of the pulmonary form of altitude sickness.

Method

Laboratory rats (Sprague Dawley rats) carried out physical activity through external stimulation for 48 hours under conditions of reduced oxygen and air pressure. Here, the air pressure was reduced to a value below 430 Torr, so that a height of over 4500 m was simulated. A prior acclimatization of the rats to the height of over 4500 m was not carried out. During this time, the rats were able to undertake a 15-20 minute pause every 4 hours in order to take in water and food. After 48 h physical activity at the simulated height of over 4500 m the rats were treated intratracheally with 300 µl/animal subject peptide SEQ ID NO: 1 (100 µg, 300 µg and 600 µg) or 300 µl saline solution. The rats then spent a further 4 hours under conditions of reduced oxygen and air pressure at the simulated height of over 4500 m. The lungs were then removed and the intensity of the pulmonary form of altitude sickness was determined (FIG. 1), the protein content in the lung fluid was determined (FIG. 2) and the histological appearance of the lung tissue was determined (FIG. 3).

Result

Figure 1:
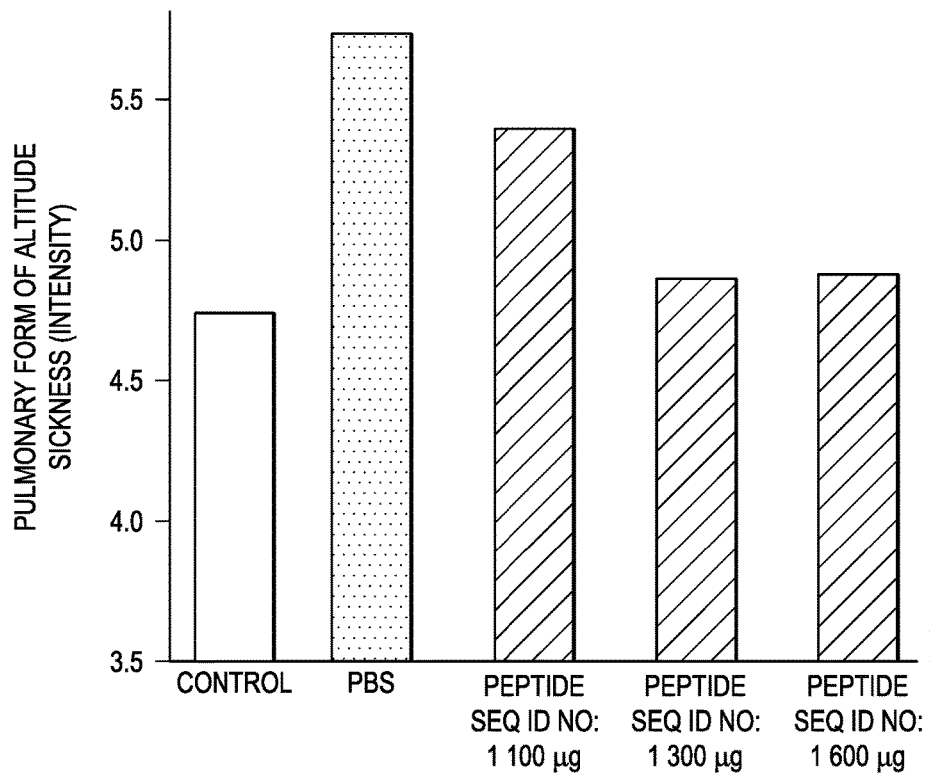
FIG. 1: The intensity of the pulmonary form of altitude sickness in rats was determined 4 hours after intratracheal administration of saline solution or respectively peptide SEQ ID NO: 1. Control: Control rates under conditions of normal oxygen and air pressure values. PBS: Rats under conditions of reduced oxygen and air pressure and intratracheal administration of saline solution. Peptide SEQ ID NO: 1 100 µg: Rats under conditions of reduced oxygen and air pressure and intratracheal administration of 100 µg peptide SEQ ID NO: 1. Peptide SEQ ID NO: 1 300 µg: Rats under conditions of reduced oxygen and air pressure and intratracheal administration of 300 µg peptide Seq. ID NO: 1. Peptide SEQ ID NO: 1 600 µg: Rats under conditions of reduced oxygen and air pressure and intratracheal administration of 600 µg peptide SEQ ID NO: 1.

The investigation showed that the intratracheal administration of peptide SEQ ID NO: 1 to laboratory rats which were exposed to the conditions of reduced air pressure and reduced oxygen concentration, led to reduction of the intensity of the pulmonary form of altitude sickness (FIG. 1). This was able to be demonstrated for 100 µg/laboratory rat and 600 µg/laboratory rat and especially for 300 µg/laboratory rat peptide SEQ ID NO: 1.

Figure 2:
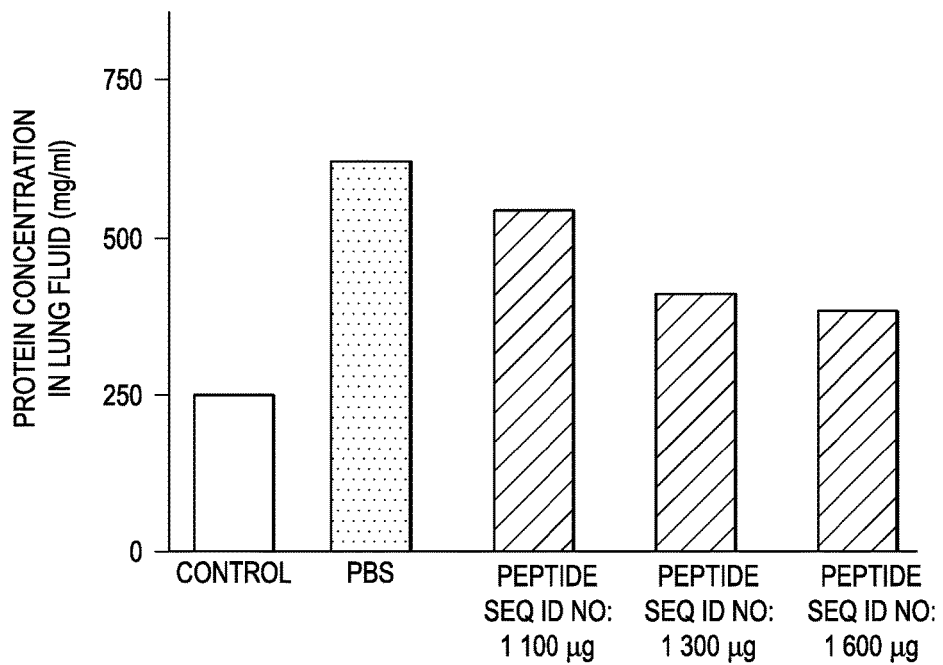
FIG. 2: The protein content in the lung fluid in rats was determined 4 hours after intratracheal administration of saline solution or respectively peptide SEQ ID NO: 1. Control: Control rats under conditions of normal oxygen and air pressure values. PBS: Rats under conditions of reduced oxygen and air pressure and intratracheal administration of saline solution. Peptide SEQ ID NO: 1 100 µg: Rats under conditions of reduced oxygen and air pressure and intratracheal administration of 100 µg peptide SEQ ID NO: 1. Peptide SEQ ID NO: 1 300 µg: Rats under conditions of reduced oxygen and air pressure and intratracheal administration of 300 µg peptide SEQ ID NO: 1. Peptide SEQ ID NO: 1 600 µg: Rats under conditions of reduced oxygen and air pressure and intratracheal administration of 600 µg peptide SEQ ID NO: 1.
Figure 3:
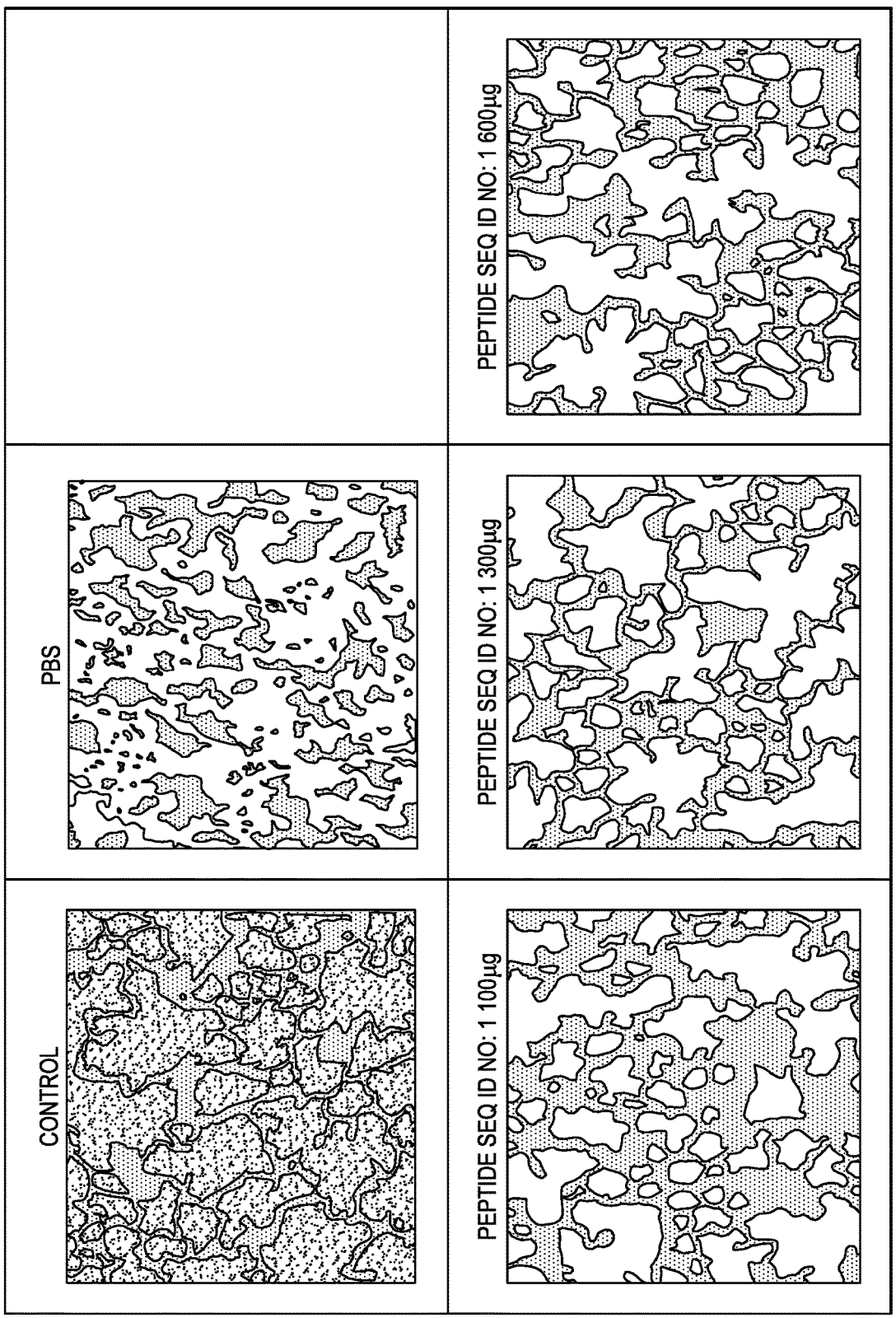
FIG. 3: Histological appearance of lung tissue in rats 4 hours after intratracheal administration of saline solution or respectively peptide SEQ ID NO: 1. Control: Control rats under conditions of normal oxygen and air pressure values. PBS: Rats under conditions of reduced oxygen and air pressure and intratracheal administration of saline solution. Peptide SEQ ID NO: 1 100 µg: Rats under conditions of reduced oxygen and air pressure and intratracheal administration of 100 µg peptide Seq. ID NO: 1. Peptide SEQ ID NO: 1 300 µg: Rats under conditions of reduced oxygen and air pressure and intratracheal administration of 300 µg peptide SEQ ID NO: 1. Peptide SEQ ID NO: 1 600 µg: Rats under conditions of reduced oxygen and air pressure and intratracheal administration of 600 µg peptide SEQ ID NO: 1.

The investigation showed, furthermore, that the intratracheal administration of peptide SEQ ID NO: 1 to laboratory rats which were exposed to the conditions of reduced air pressure and reduced oxygen concentration, led to reduction of the protein concentration in the lung fluid (FIG. 2). This was able to be demonstrated for 100 µg/laboratory rat and 600 µg/laboratory rat and especially for 300 µg/laboratory rat peptide SEQ ID NO: 1.

The histological examination showed that the rats treated with saline solution exhibited swollen lung tissue with erythrocytes, with the lung tissue in rats after administration of peptide SEQ ID NO: 1 being comparable with healthy lung tissue of the control rats, which were not exposed to the conditions of reduced oxygen and air pressure.

EXAMPLE 2 ex vivo assessment of the pro-inflammatory characteristics of the peptide according to the invention with SEQ ID NO: 1 in human whole blood.

A pharmacological ex vivo safety study was carried out with regard to the peptide SEQ ID NO: 1 according to the invention in human full blood, in order to establish whether the peptide SEQ ID NO: 1 leads to the release of the pro-inflammatory marker interleukin-6 (IL-6) from fresh full blood (i.e. whether or not peptide SEQ ID NO: 1 shows TNF-specific inflammatory activity (i.e. TNF receptor binding activity)). In this study, fresh full blood was used; this is a recognized prediction model for the assessment of the inflammatory reaction in vivo.

Summary of the Methodology

The aim of this study was to determine the pro-inflammatory signal capacity of the peptide SEQ ID NO: 1. Here, full blood cultures were used and the secretion of interleukin-6 (IL-6), a very sensitive marker for pro-inflammatory stimulation, was quantified by means of ELISA.

Test System 25 ml heparinised blood freshly taken from 5 healthy subjects (HS) was used in the tests.

Test Object

Identification: Peptide SEQ ID NO: 1 (Dose: 1 ng/ml to 10 µg/ml; single administration in solution)

Description: White powder, purity 96%

Full Blood Cultures

Full blood (FB) cultures were carried out by pipetting 1 ml FB in depressions of 24-well plates. In each experiment, unstimulated and stimulated control cultures were included.

If possible, the substances and stimulants to be examined were always used in the same volume in each well in a given experiment, which is not greater than 10% of the total volume in a well. Unstimulated controls took place with PBS. Volume adjustment and dilutions for different treatments were likewise carried out with PBS.

The content of each well was mixed and the plates were incubated at 37° C. and 5% $CO_2$ for 24 hours. After incubation, the content of each well was transferred into a fresh 1.5 ml microtube and centrifuged at 8000 to 9000×g for 15 minutes. The supernatant of each sample was divided individually to two 1.5 ml reaction vessels and stored at −20° C. until use.

Analysis of Interleukin-6

Interleukin-6 was quantified by means of a specific ELISA (Human IL-6 ELISA-Set, BD Biosciences, Cat. No. 555220) using an anti-human-IL-6 antibody as capture antibody, a biotinylated anti-human IL-6 detection antibody, avidin horseradish peroxidise conjugate as enzyme reagent and recombinant IL-6 as standard. Absorption measurement at 450 nm was carried out with the Packard Fusion reader.

Data Analysis

The results of each plate were stored and evaluated with the fusion data analysis software.

Summary of the Results of the Study

The aim of this study was to determine the pro-inflammatory signalling capacity of the peptide SEQ ID NO: 1. Full blood cultures were used and the secretion of IL-6, a very sensitive marker for inflammatory pro-stimulation, was quantified by means of ELISA.

Full blood samples of five healthy subjects were either left unstimulated (negative control), stimulated with high and low doses of LPS (positive controls) or incubated with the peptide in nine semi-logarithmic dilutions of 10 µg/ml to 1 ng/ml. The results are presented in the following table:

Table: Release of Interleukin-6 from Fresh Full Blood with Addition of Peptide SEQ ID NO: 1 and LPS Peptide SEQ ID NO: 1 Positive control (LPS)
Concentration Concentration of IL-6 (pg/ml, n=5)

| | | |
|---|---|---|
| 0 (Negative Control) | less than 0.5 | less than 0.5 |
| 10 mg/ml | less than 0.5 | 195.640 |
| 1 mg/ml | less than 0.5 | 108.370 |
| 3 ng/ml | less than 0.5 | 34.867 |
| 1 ng/ml | less than 0.5 | not determined |

The results clearly show that the peptide SEQ ID NO: 1 did not induce any detectable amount of IL-6 secretion in any of the tested concentrations. The positive controls (LPS) led to an intensive induction of the IL-6 secretion.

Discussion

The experiments were carried out in order to establish whether the peptide SEQ ID NO: 1 brings about the induction of a pro-inflammatory cascade. The readout parameter was the induced secretion of IL-6 in full blood cultures from five healthy donors. The results clearly showed that the peptide SEQ ID NO: 1 induced no detectable level of IL-6 in the donor cultures. It is therefore demonstrated that the peptide SEQ ID NO: 1 does not induce a pro-inflammatory response in the selected ex vivo model and therefore does not have TNF receptor binding activity. This test can be applied for any variants of the peptide according to the invention, in order to establish the feature of freedom from TNF receptor binding activity.

EXAMPLE 3

Assessment of the bioactivity of the peptide according to the invention compared with the non-cyclized (and therefore not according to the invention) form of the peptide and other synthetic peptides which have been proposed in the prior art for the treatment of oedemas, in a patch clamp assay with A549 cells.

Summary:

In this example, the biological activity of the peptide according to the invention was assessed with three other synthetic peptides with regard to the capability for induction of the sodium flow. The synthetic comparative peptides were also proposed in European Patent Application EP 2 009 023 A1 as peptides for the treatment of oedemas. For these peptides, it was assumed in EP 2 009 023 A1 that they would be able to inhibit or reduce the accumulation of excess fluid in tissues. In EP 2 009 023 A1 this characteristic was investigated by means of the TEER test; within the present example, this biological activity is investigated in a whole cell patch clamp test with A549 cells.

This measurement principle (whole cell patch clamp test) reflects the fluid balance in the human lung significantly better and is therefore a recognized test system for this question. The fluid balance in the healthy adult human lung depends on ion transport mechanisms which lead via the lung epithelium, with the participation of $Na^+$ transporter in the clearance of alveolar fluid having been documented in several studies. In particular here, the amiloride-sensitive epithelial sodium ion channel (ENaC) of type II alveolar cells was identified as main regulator of the clearance of alveolar fluid.

In order to assess the activity of the amiloride-sensitive epithelial sodium ion channel (ENaC) and to determine its activation by biological and chemical compounds, the whole cell patch clamp technique was established as the experimental methodology of choice for the measurement of the sodium ion movement via the apical membrane of alveolar cells to predict the clearance of alveolar fluid.

Accordingly, in the present example the biological activity of the peptide according to the invention and of three synthetic peptides, QRETPEGAEAKPWY (SEQ ID No: 3, described in the prior art as suitable for the treatment of oedemas, is, however, in contrast to the form according to the invention, not cyclized in this experiment), TKPIELGPDEPKAV (SEQ ID NO: 16; described in the prior art as suitable for the treatment of oedemas, is, however, in contrast to the peptides according to the invention, not cyclized and does not contain the core sequence $TX_1EX_2X_3E$ or respectively TPEGAE) and CGTKPIELGPDEPKAVC (SEQ ID NO: 17; described in the prior art as suitable for the treatment of oedemas, however, in contrast to the peptides according to the invention, does not contain the core sequence $TX_1EX_2X_3E$ or respectively TPEGAE) was determined by means of whole cell patch clamp measurements on A549 cells, a continuous cell line of human alveolar type II cells.

It was shown here that none of the peptides QRETPEGAEAKPWY (SEQ ID NO: 18), TKPIELGPDEPKAV (SEQ ID NO: 76) and CGTKPIELGPDEPKAVC (SEQ ID NO: 2), although related from their primary sequence with the peptides provided according to the invention, had any effect on the sodium flow and therefore also no activating effect on the amiloride-sensitive epithelial sodium ion channel (ENaC), whereas the peptide according to the invention induced an increase of the sodium flow over that of the control value, when it was added to the bath solution in a whole cell patch clamp test using A549 cells. As therefore the three comparative peptides showed no effect on the amiloride-sensitive epithelial sodium ion channel (ENaC), compared with the positive control (peptide according to the invention with SEQ ID NO: 1; CGQRETPEGAEAKPWYC (SEQ ID NO: 1)) in a whole cell patch clamp test using A549 cells, the clearance of alveolar fluid is, however, a consequence of this sodium ion movement over the alveolar epithelial cells, it can be concluded that these peptides according to the prior art—in contrast to the peptide according to the invention—are not able to reduce lung oedemas, although respectively particularly preferred variants both of the linear and also of the cyclic peptides which are described in EP 2 009 023 A1 were investigated in the present example (QRETPEGAEAKPWY (SEQ ID NO: 18), TKPIELGP-DEPKAV (SEQ ID NO: 76) and CGTKPIELGPDEPKAVC (SEQ ID NO: 2), which are indicated as peptides SEQ ID NO: 18, SEQ ID NO: 76 and SEQ ID NO: 2 in EP 2 009 023 A1). This is all the more remarkable, since an activity in the combating of oedemas was attributed to the comparative peptides in EP 2 009 023 A1.

This shows on the one hand that the features provided according to the invention, in particular the cyclizing and the core sequence $TX_1EX_2X_3E$ or respectively TPEGAE, are essential features of the present invention. On the other hand, the present investigations also justify scientifically corroborated doubts regarding the assumption that these peptides themselves are suitable for the oedema treatment proposed in the prior art. The present example, which was carried out by the test system of the whole cell patch clamp test, which is recognized in the specialist scientific world, shows namely that the investigation system (the TEER test) used in EP 2 009 023 A1 is evidently not suitable to prove this activity.

Introduction:

The fluid balance in the healthy adult human lung depends on ion transport mechanisms over the lung epithelium, wherein the participation of the $Na^+$ transporters in the clearance of the alveolar fluid is well documented. In particular here the amiloride-sensitive epithelial $Na^+$ channel (ENaC) represents a limiting step for the $Na^+$ reception over the alveolar epithelium and plays the key role in fluid reabsorption in the lung. As an improved clearance of alveolar fluid leads directly to an improved prognosis and restoration in the case of a lung oedema, the improvement of the ENaC activity offers a promising therapeutic option for the treatment of lung oedemas.

European patent application EP 2 009 023 A1 proposes for this peptides such as QRETPEGAEAKPWY, TKPIELGPDEPKAV and CGTKPIELGPDEPKAVC (described there as peptides SEQ ID NO: 18, SEQ ID NO: 76 and SEQ ID NO: 2) as new molecules which are to inhibit or reduce the accumulation of excess fluid in the tissue.

According to patent application EP 2 009 023 A1, the so-called transepithelial electrical resistance (TEER) test was used for the screening of anti-lung oedema active ingredient candidates. The "TEER test" is not an established test for the prediction of fluid clearance in lung oedemas (this test can not be found in the relevant scientific literature and also has no relevance with regard to the cells being used (Calu-3 cells) in a model for gas exchange in the human lung). In the present example—in addition to the peptide according to the invention—the peptides QRETPEGAEAK-PWY, TKPIELGPDEPKAV and (cyclized) CGTKPIELGP-DEPKAVC were investigated by means of a whole cell patch clamp assay, an established methodology for the measurement of ion movement over the cell membranes and especially for the measuring of the sodium transport over the cell membrane of alveolar epithelial cells (Eaton et al., Fed. Proc. 45 (1986), 2707; Hamill et al., Pflugers Arch. 391 (1981) 85-100. Here it was to be tested whether or not the peptides can activate the amiloride-sensitive epithelial sodium flow in lung cells.

The "TEER test", as it has been described in EP 2 009 023 A1, uses cell layers of Calu-3 cells. However, Calu-3 cells are bronchial cells. Bronchial cells represent approximately 1% of the surface of the human lung for gas exchange and therefore do not represent an appropriate model for alveolar epithelial cells, which form approximately 99% of the surface of the human lung for gas exchange. In the present example, the human alveolar epithelial cell line A549 was used, because this cell line defines the generally accepted experimental standard and is regarded in the literature as the model of choice for alveolar epithelial cells (Lazrak et al., Am. J. Physiol. Lung Cell. Mol. Physiol. 278 (2000), 848-857).

Experimental Procedure

Peptides Investigated

Peptide "AP301" (peptide according to the invention): Cyclo-H-Cys-Gly-Gln-Arg-Glu-Thr-Pro-Glu-Gly-Ala-Glu-Ala-Lys-Pro-Trp-Tyr-Cys-OH (SEQ ID NO: 1)

Synthetic peptide QRETPEGAEAKPWY:
H-Gln-Arg-Glu-Thr-Pro-Glu-Gly-Ala-Glu-Ala-Lys-Pro-Trp-Tyr-OH
(SEQ ID NO: 3, described in the prior art as suitable for the treatment of oedemas, is, however, in contrast to the form according to the invention, not cyclized in this experiment)

Synthetic peptide TKPIELGPDEPKAV:
H-Thr-Lys-Pro-Ile-Glu-Leu-Gly-Pro-Asp-Glu-Pro-Lys-Ala-Val-OH
(SEQ ID NO: 16; described in the prior art as suitable for the treatment of oedemas, is, however, in contrast to the peptides according to the invention, not cyclized and does not contain the core sequence $TX_1EX_2X_3E$ or respectively TPEGAE)

Synthetic peptide CGTKPIELGPDEPKAVC:
Cyclo-H-Cys-Gly-Thr-Lys-Pro-Ile-Glu-Leu-Gly-Pro-Asp-Glu-Pro-Lys-Ala-Val-Cys-OH (SEQ ID NO: 17; described in the prior art as suitable for the treatment of oedemas, however, in contrast to the peptides according to the invention, does not contain the core sequence $TX_1EX_2X_3E$ or respectively TPEGAE).

Peptide Synthesis

All peptides in the present example were produced by solid phase peptide synthesis according to the fluorenylmethyloxycarbonyl/t-butyl protection strategy on 2-chlorotritylchloride resin. Diisopropylcarbodiimide and N-hydroxybenzotriazole were used as coupling reagents. All coupling steps were carried out in N—N-dimethylformamide. Protected amino acids were coupled in succession to the peptide chain, beginning with the C-terminal amino acid. Deprotection of the fluorenylmethyloxycarbonyl was carried out in 20% piperidine in N—N-dimethylformamide. Separation of the completed, partially protected peptide from the resin was carried out in a 1:1 mixture of acetic acid and dichloromethane.

In the case of the peptide SEQ ID NO: 1, after separation from the resin, the side chain deprotection was carried out in 95% trifluoroacetic acid, 5% water, followed by cyclizing of the linear raw peptide by oxidation of the terminal cysteine residues by the supply of oxygen ($O_2$ at 1.2 bar) at pH 8.5 for approximately 100 hours.

The raw peptide product was purified by reverse phase medium pressure liquid chromatography (RP-MPLC) on a RP-C18 silica gel column with a gradient of 5%-40% acetonitrile. Finally, the trifluoroacetate counterion was replaced by acetate on a Lewatit MP64 column (acetate form). After a final washing step in water, the purified peptide was lyophilised as acetate salt and obtained as a white to cream-coloured powder. In the case of peptide 2, the intermolecular disulphide bridge caused problems in the separation from the Lewatit column, therefore this cyclic peptide was used in the trifluoroacetate form instead of the acetate form.

Characterization of the Peptides

The molecular masses of the peptides were confirmed by electrospray ionization mass spectrometry or MALDI-TOF-MS; the purity was determined by analytical high performance liquid chromatography.

The peptides were stored at −20° C.

Patch Clamp Protocol

The whole cell patch clamp test using A549 cells took place as described in Hazemi et al. (J. Med. Chem. 53 (2010), 8021-8029). Solutions of the peptides were added to the external (bath) solution in the patch clamp test, so that a final concentration of 300 nM was reached. In cases where an increase of the flow after addition of a given peptide was observed, an amiloride solution (to 100 mM final concentration) was added to the bath solution—after the flow reached a stationary state —, in order to differentiate the amiloride-sensitive from the amiloride-insensitive flow. The amiloride-sensitive flow was then calculated by subtracting the flow value after addition of amiloride (amiloride-insensitive) from the flow value of the stationary state before the addition of amiloride. For each peptide, three experiments were carried out in different A549 cells (n=3).

Results

Figure 4:
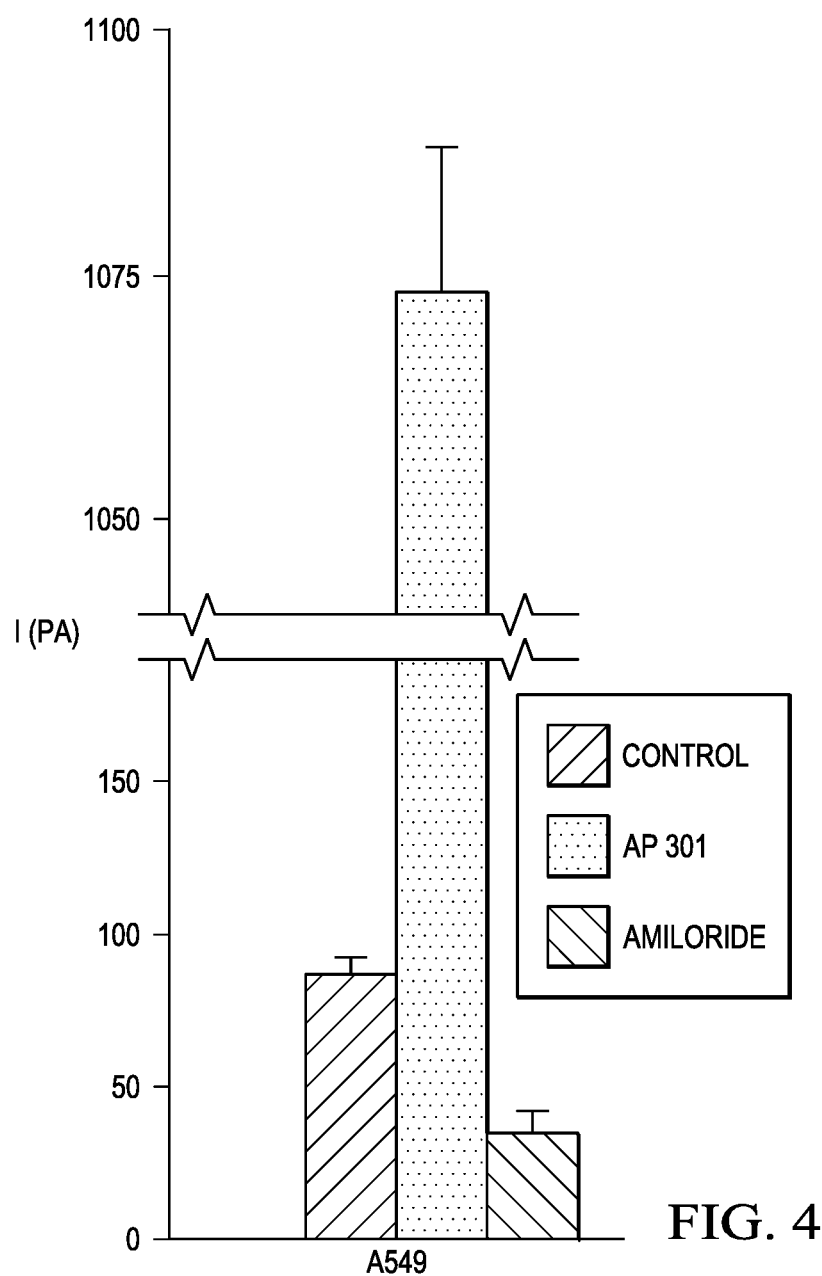
FIG. 4: Mean values of the inwardly flowing $Na^+$ flows in A549 cells, in a whole cell patch clamp test during the control phase at −100 mV clamped, after addition of PEPTIDE SEQ ID NO: 1 ("AP301") (240 nM) and after addition of amiloride (100 mM) to the bath solution. The values are mean values+/−SE.

The peptide according to the invention; SEQ ID NO: 1 ("AP301"); positive control peptide) led, when it was added to the bath solution in a whole cell patch clamp test using A549 cells in a final concentration of 240 nM, to an increase of the active $Na^+$ flow from a control value of 86 pA±5 pA (before addition of AP301) to a maximum of 1073±15 pA (after addition of AP301). The subsequent addition of amiloride caused a reversion of the flow to 36 pA±5 pA. This showed that the flow which has been increased by AP301 is the amiloride-sensitive $NA^+$ flow (FIG. 4).

Figure 5:
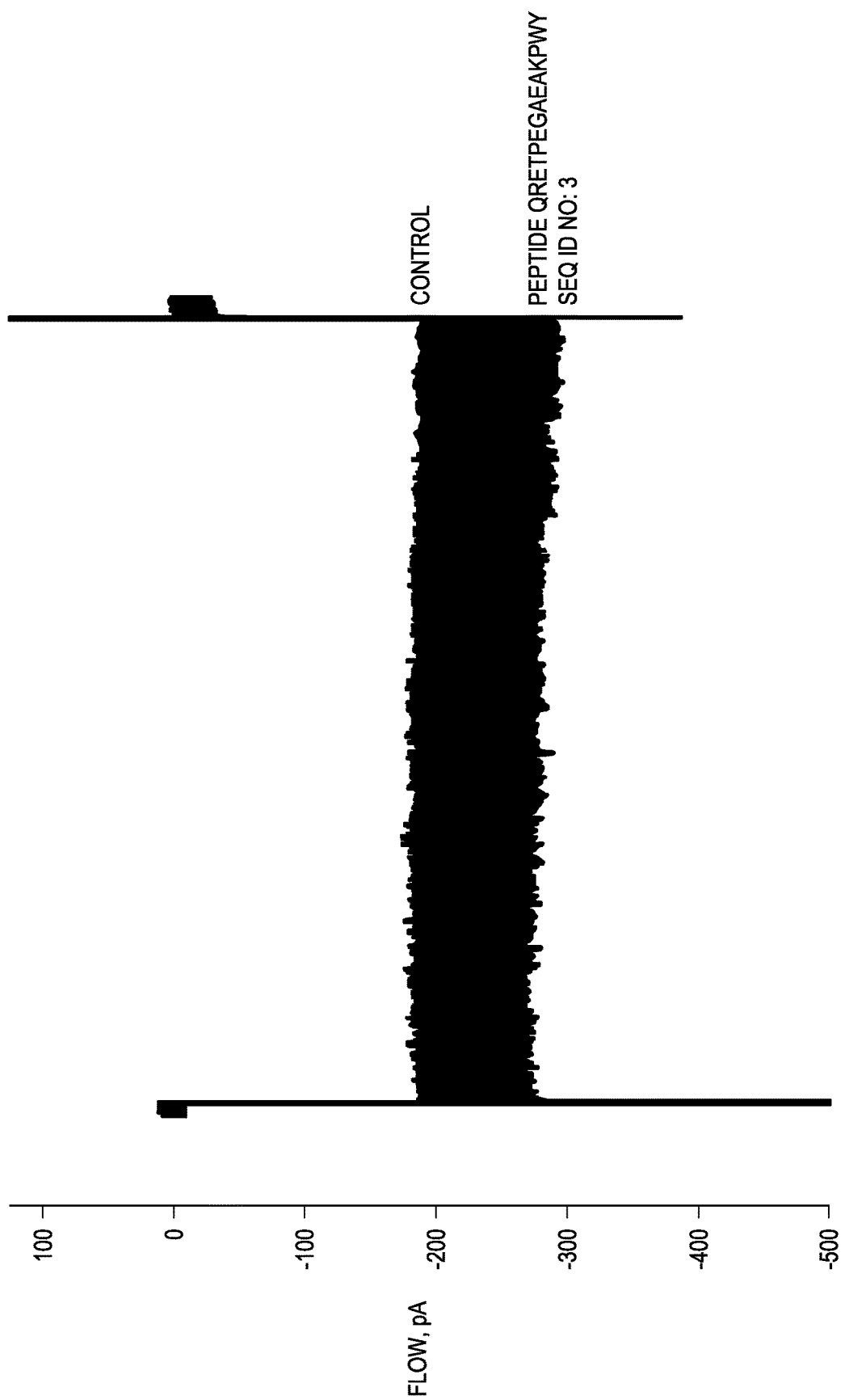
FIG. 5: Action of the synthetic peptide QRETPEGAEAKPWY (SEQ ID NO: 3, described in the prior art as suitable for the treatment of oedemas, is, however, in contrast to the form according to the invention, not cyclized in this experiment) on the $Na^+$ flow in an A549 cell patched in whole cell mode. Representative original recording of a cell clamped at a holding potential of −100 mV during the control phase and after addition of the peptide QRETPE-GAEAKPWY (300 nM) in the bath solution.
Figure 6:
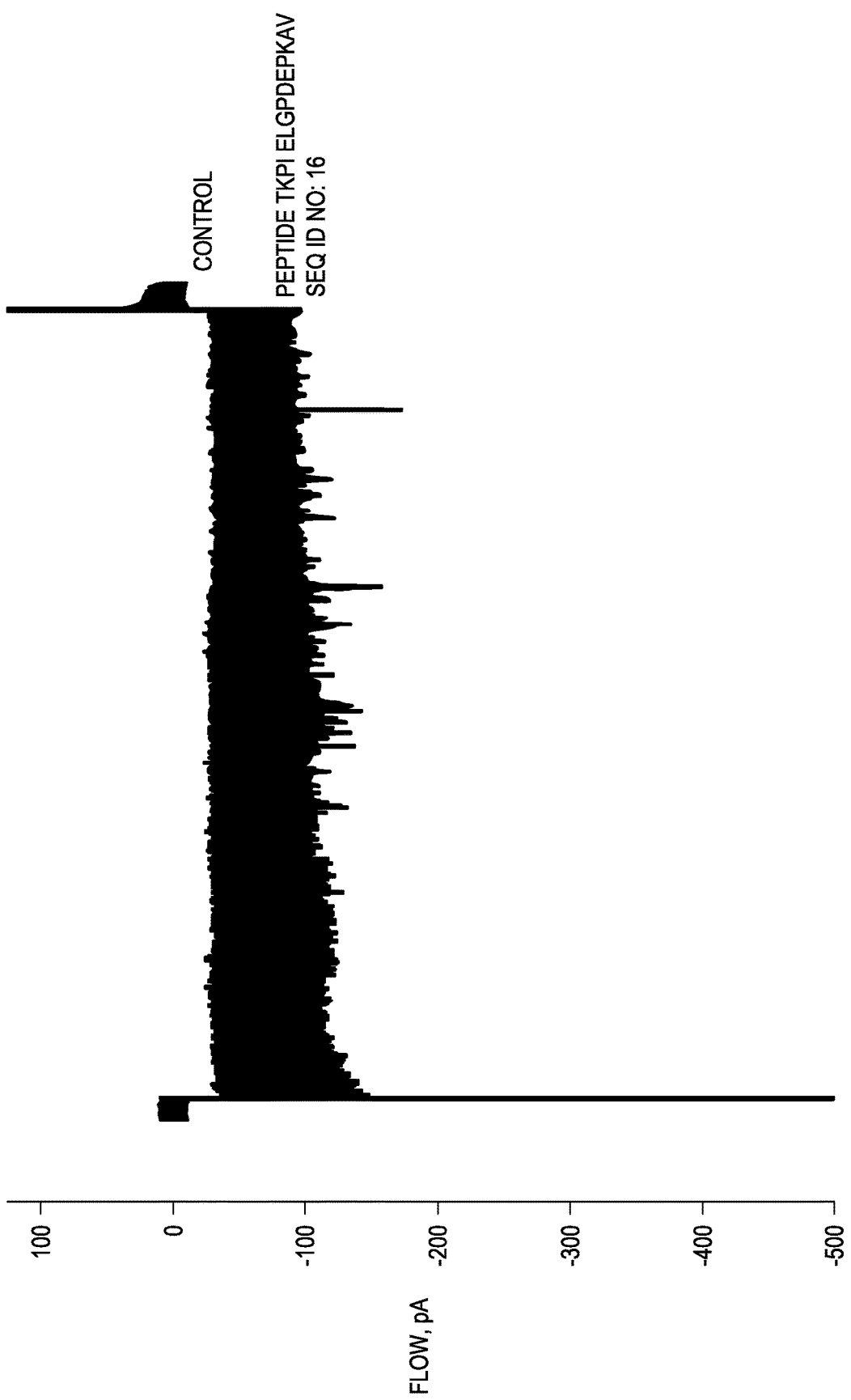
FIG. 6: Action of the synthetic peptide TKPIELGPDEPKAV (SEQ ID NO: 16; described in the prior art as suitable for the treatment of oedemas, is, however, in contrast to the peptides according to the invention, not cyclized and does not contain the core sequence $TX_1EX_2X_3E$ or respectively TPEGAE) on the $Na^+$ flow in an A549 cell patched in the whole cell mode. Representative original recording of a cell clamped at a holding potential of −100 mV during the control phase and after addition of the peptide TKPIELGPDEPKAV (300 nM) in the bath solution.
Figure 7:
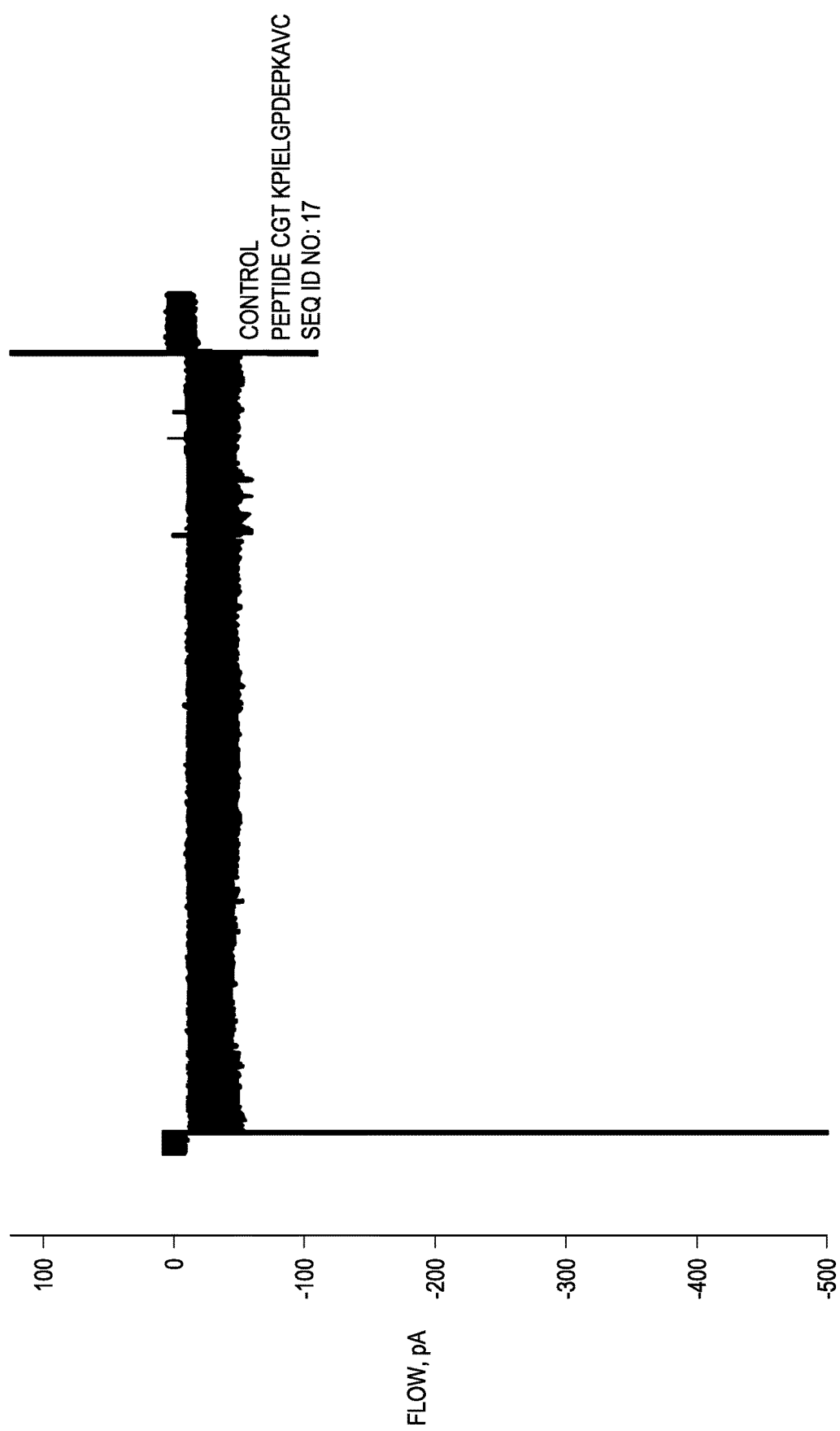
FIG. 7: Action of the synthetic cyclic peptide CGTKPIELGPDEPKAVC (SEQ ID NO: 17; described in the prior art as suitable for the treatment of oedemas, however, in contrast to the peptides according to the invention, does not contain the core sequence $TX_1EX_2X_3E$ or respectively TPEGAE) on the $Na^+$ flow in an A549 cell patched in the whole cell mode. Representative original recording of a cell clamped at a holding potential of −100 mV during the control phase and after addition of the cyclic peptide CGTKPIELGPDEPKAVC (300 nM) in the bath solution.

When the three synthetic comparative peptides, QRETPEGAEAKPWY, TKPIELGPDEPKAV and CGTKPIELGPDEPKAVC were added in separate whole cell patch clamp experiments using A549 cells to the bath solution in a final concentration of 300 nM, no effect on the flow was able to be observed: the values remained in the range of the control value (FIGS. 5-7).

Discussion of the Results

In the present example, the capability was shown of the peptide according to the present invention ("AP301") as positive control in the increase of the amiloride-sensitive $Na^+$ flow in a whole cell patch clamp test with A549 cells. Addition of AP301 to the bath solution led to an increase of the flow proceeding from a control value of 86 pA±5 pA (before addition of AP301) to a maximum of 1073±15 pA (after addition of AP301). The subsequent addition of amiloride caused a reversion to 36 pA±SpA. This shows that AP301 increases the amiloride-sensitive $Na^+$ flow of 50 pA to 1037 pA and therefore confirms the activating effect of AP301 on the amiloride-sensitive epithelial $Na^+$ channel (ENaC) (cf. also Tzotzos et al., Pulm. Pharmacol. Ther. 26 (2013), 356-363), which is arranged in the lung apically in alveolar epithelial cells. Activation of ENaC leads to an increase of the $Na^+$ reception from the alveolar fluid into the epithelial layer, so that the osmotic driving force is increased, which underpins the clearance of alveolar fluid and leads to water flowing from the alveoli into the interstitial layer under the epithelium. The mechanism which forms the basis of the observed alveolar fluid clearing effect of AP301 administered directly to the lung could be due to this.

Each of the three other synthetic comparative peptides, QRETPEGAEAKPWY, TKPIELGPDEPKAV and CGTK-PIELGPDEPKAVC was likewise tested for the capability of influencing the $Na^+$ flow when it was added to the bath solution in a whole cell patch clamp test with A549 cells. However, unlike AP301, which showed an immediate intensifying effect, none of the other three peptides had an influence on the flow in these cells, even in a somewhat higher application concentration than the peptide AP301 according to the invention (300 nM for the three peptides, 240 nM for AP301).

EXAMPLE 4

Activation of the Amiloride-Sensitive Sodium Ion Channel (EnaC) by the Peptides According to the Invention The peptides SEQ ID NOS: 1 and 11 to 15 according to the invention were characterized extensively in cell-based studies. These cyclic peptides SEQ ID NOS: 1 and 11 to 15 activate the amiloride-sensitive sodium ion channel (ENaC) in lung cells. Thereby, the equivalency of these peptides with the previously investigated AP301 in the effect according to the present invention is clarified.

Peptide Sequences

SEQ ID NO: 1: CGQRETPEGAEAKPWYC: The cyclizing of the peptide was achieved in that the terminal cysteines (C) were oxidized with the development of a sulphur bridge.

SEQ ID NO: 11: KSPGQRETPEGAEAKPWYE: In the cyclic peptide SEQ ID NO: 11 the amino acids are linked peptidically from the C-terminal amino acid glutamic acid (E) to the N-terminal amino acid lysine (K), whilst the N-terminal amino acid lysine (K) is connected with the C-terminal amino acid glutamic acid (E) by means of an amide bond between the nitrogen of the epsilon amino group of the side chain of the lysine and the gamma carbon in the side group of the glutamic acid.

SEQ ID NO: 12: KGQRETPEGAEAKPWYG: In the cyclic peptide SEQ ID NO: 12 the amino acids are linked peptidically from the C-terminal amino acid glycine (G) to the N-terminal amino acid lysine (K), whilst the N-terminal amino acid lysine (K) is connected with the C-terminal amino acid glycine (G) by means of an amide bond between the nitrogen of the epsilon amino group of the side chain of the lysine and the carbon of the carboxyl group of the glycine.

SEQ ID NO: 13: Ornithine-GQRETPEGAEAKPWYG: In the cyclic peptide SEQ ID NO: 13 the amino acids are linked peptidically from the C-terminal amino acid glycine (G) to the N-terminal amino acid ornithine (Orn), whilst the N-terminal amino acid ornithine (Orn) is connected with the C-terminal amino acid glycine (G) by means of an amide bond between the nitrogen of the delta amino group of the side chain of the ornithine and the carbon of the carboxyl group of the glycine.

SEQ ID NO: 14: 4-aminobutanoic acid-GQRETPEGAE-AKPWYD: In the cyclic peptide SEQ ID NO: 14 the amino acids are linked peptidically from the C-terminal aspartic acid (D) to the N-terminal amino acid glycine (G), whilst the C-terminal aspartic acid (D) is connected with the N-terminal amino acid glycine by means of an amide bond between the nitrogen of the amino group of the N-terminal glycine and the carbon C1 of the carboxyl group of the 4-aminobutyric acid on the one hand, and by means of an amide bond between the nitrogen of the amino group of the 4-aminobutyric acid and the carbon of the carboxyl group of the side chain of the C-terminal aspartic acid on the other hand.

SEQ ID NO: 15: β-alanine-GQRETPEGAEAKPWYE: In the cyclic peptide SEQ ID NO: 15 the amino acids are linked peptidically from the C-terminal glutamic acid (E) to the N-terminal amino acid glycine (G), whilst the C-terminal glutamic acid (E) is connected with the N-terminal amino acid glycine by means of an amide bond between the nitrogen of the amino group of the N-terminal glycine and the carbon C1 of the carboxyl group of the β-alanine on the one hand, and by means of an amide bond between the nitrogen of the amino group of the β-alanine and the carbon of the carboxyl group of the side chain of the C-terminal glutamic acid on the other hand.

SEQ ID NO: 19: CGQREAPAGAAAKPWYC (not according to the invention): The cyclizing of the peptide SEQ ID NO: 19 was achieved in that the terminal cysteines (C) were oxidized with the development of a sulphur bridge.

Peptide Synthesis

The cyclic peptides SEQ ID NOS: 1, 11 to 15 and 19 were produced by means of Fmoc solid phase synthesis fully automatically, with adherence to the following steps: sequential coupling of the amino acids; selective separating from the solid phase; purification and lyophilisation, selective cyclizing; separating of the protective groups; purification and lyophilisation; analytical examination.

The cyclic peptides SEQ ID NOS: 1 and 11 to 15 (according to the invention) and 19 (not according to the invention) were then examined for purity and mass by means of reverse HPLC.

The purity of the cyclic peptide SEQ ID NO: 1 was 96.3% m/z (ESI) 1924.2 (M++1). The purity of the cyclic peptide SEQ ID NO: 11 was 96.3%. m/z (ESI) 1924.1 (M++1). The purity of the cyclic peptide SEQ ID NO: 12 was 98.8%. m/z (ESI) 1888.2 (M++1). The purity of the cyclic peptide SEQ ID NO: 13 was 97.4%. m/z (ESI) 1873.4 (M++1). The purity of the cyclic peptide SEQ ID NO: 14 was 99%. m/z (MALDI-TOF) 1901.6 (M++1). The purity of the cyclic protein SEQ ID NO: 15 was 99%. m/z (MALDI-TOF) 1902.7 (M++1). The purity of the cyclic peptide SEQ ID NO: 19 was 95%. m/z (MALDI-TOF) 1778.02 (M++1).

All the peptides according to the invention SEQ ID NOS: 1 and 11 to 15 have the following shared structural characteristic:

Sequence: $X_1$-GQRETPEGAEAKPWY-$X_2$ (SEQ ID NO: 21)

where $X_1$ represents an amino acid or 1 to 4 amino acids, in particular 1 or 3 amino acids, where the amino acids are natural or unnatural amino acids, where $X_1$ represents the amino acid C, K, ornithine, 4-aminobutyric acid, β-alanine, or the sequence KSP, where $X_2$ may be a natural or unnatural amino acid, where $X_2$ may be the amino acid C, D, G or E, and where $X_1$ is the N-terminal amino acid and $X_2$ is the C-terminal amino acid.

Electrophysiological Investigations of the Amiloride-Sensitive Sodium Ion Channel (ENaC)

Macroscopic sodium ion flows were derived from human lung epithelial cells A549 with the "whole cell" configuration by means of the "patch clamp" technique (Hamill et al., Pflugers Arch. 391 (1981), 85-100). For the flow derivations in the "whole cell" configurations the following bath- and electrode solutions were used:

Bath solution: 135 mM sodium methanesulphonate, 10 mM NaCl, 2.7 mM KCl, 1.8 mM $CaCl_2$, 2 mM $MgCl_2$, 5.5 mM glucose, and 10 mM HEPES, pH 7.4.

Electrode solution: 120 mM potassium methanesulphonate, 15 mM KCl, 6 mM NaCl, 1 mM $Mg_2ATP$, 2 mM Na3ATP, 10 mM HEPES, and 0.5 mM EGTA (pH 7.2).

Coverslips with the cells cultivated thereon were transferred into an experimental bath holding 1 ml, were fixed on the microscope table (Axiovert 100, 400× magnification) and the cells were superfused with the bath solution described above. The flow was then derived from a suitable cell (which adheres to the coverslip). For this, a microelectrode (glass capillary with a defined, heat-polished tip opening of approx. 1-3 µm, corresponds to a resistance of the electrode tip of 3-5 MΩ) filled with an electrolyte solution was placed onto the cell and the membrane was suctioned, so that a "Gigaohm seal" was formed between membrane and electrode, in order to minimize the leakage current. With the "whole cell configuration" the membrane was penetrated under the electrode tip, so that the flow, which flows through all ion channels of the cell, can be measured. On obtaining a "Gigaohm seal", a defined membrane holding potential was applied via a pre-amplifier (CV-4 Headstage, Axon Instruments) and amplifier (Axopatch 1D, Axon Instr.) and the flow, which flows here through the ion channels, was measured.

The pulse protocol consisted of a hyperpolarisation of the cell membrane to −100 mV for 5 s and subsequent incremental depolarisation in 20 mV stages to +100 mV.

This protocol was carried out before (control) and after addition of the cyclic proteins. The flow derivations which were thus obtained were stored and analysed by means of the PCLAMP 6.0 programme. For this, the flow derivations obtained in the presence of amiloride were subtracted from the previously registered flows, so that the amiloride-sensitive sodium flow through the epithelial sodium channels was able to be determined.

The results of the measurements are summarized in Table 1. The activity of the individual peptides is indicated as EC50 (in nM). The EC50 is the effective concentration at which 50% of the maximum activity (i.e. maximum increase of flow intensity, I) is measured.

Table 1. Activity of the peptides according to the invention SEQ ID 1 and SEQ ID 11-15, and of the peptide SEQ ID NO: 19 not according to the invention, on the cellular amiloride-sensitive sodium ion flow. The activity is indicated as effective concentration at 50% of the maximum activity ($EC_{50}$).

| Cyclic Peptide | $EC_{50}$ (nM) |
| --- | --- |
| SEQ ID NO: 1 | 54 |
| SEQ ID NO: 11 | 56 |
| SEQ ID NO: 12 | 38 |
| SEQ ID NO: 13 | 45 |
| SEQ ID NO: 14 | 24 |

| Cyclic Peptide | EC$_{50}$ (nM) |
|---|---|
| SEQ ID NO: 15 | 19 |
| SEQ ID NO: 19 | No activity |

Figure 8:
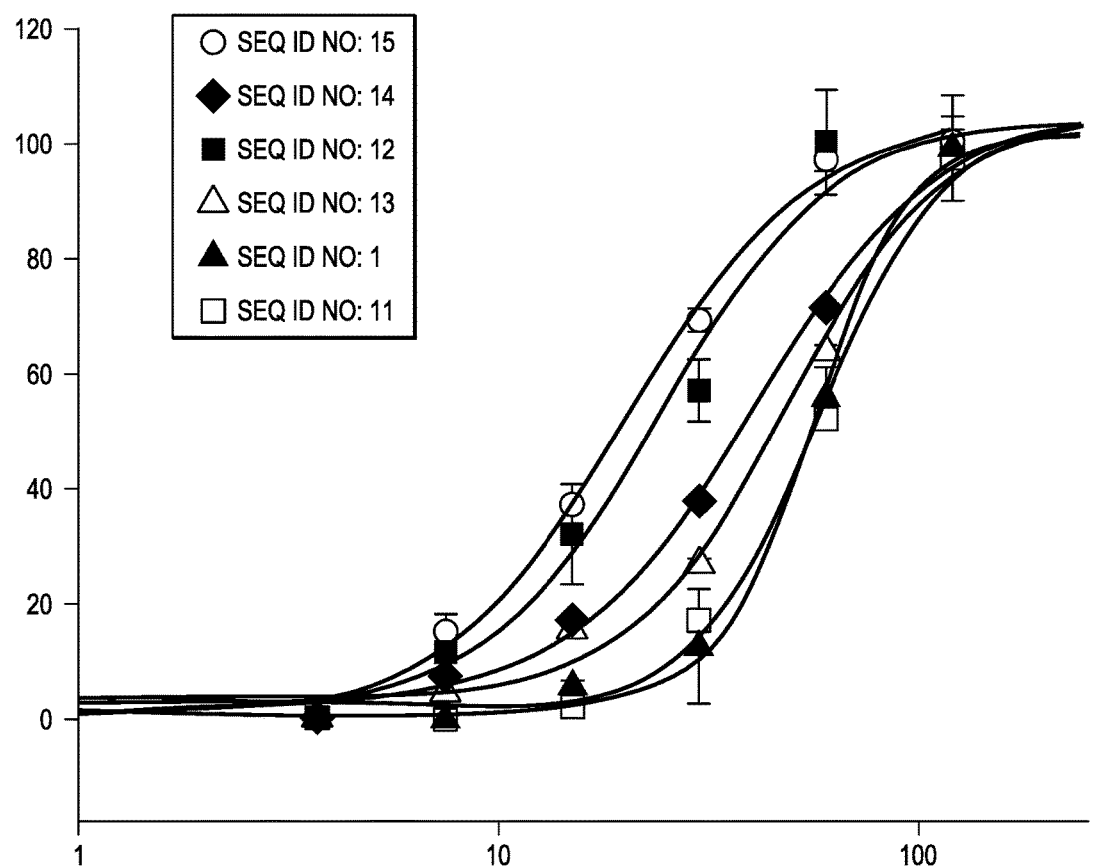
FIG. 8: Activity of the cyclic peptides SEQ ID NOS: 1 and 11 to 15 as a function of the concentration. On the x-axis the concentration is entered in a logarithmic scale in nM; on the y-axis the sodium ion flow is entered (in %).

The activity of the cycle peptides SEQ ID NOS: 1 and 11 to as a function of the concentration is presented in FIG. 8. The maximum activity was indicated by 100%.

The illustrated investigations show that the peptides SEQ ID NOS: 1 and 11 to 15 according to the invention are biologically active, whereas the peptide SEQ ID NO: 19 not according to the invention is not active. The difference between the cyclic peptides SEQ ID NOS: 1 and 11 to 15 and the cyclic peptide SEQ ID NO: 19 consists in that within the general peptide sequence X$_1$-GQRETPEGAEAKPWY-X$_2$ the amino acid T (at 5$^{th}$ position) and the amino acid E (at 7$^{th}$ position) and the amino acid E (at 10$^{th}$ position) were exchanged by alanine. The sequence TPEGAE is therefore essential. The structure of X$_1$ and X$_2$ have no essential influence on the activity.

Summary of the Sequences:

```
                                                     SEQ ID NO: 1
CGQRETPEGAEAKPWYC

SEQ ID NO: 2
TPEGAE

SEQ ID NO: 3
QRETPEGAEAKPWY

SEQ ID NO: 4
PKDTPEGAELKPWY

SEQ ID NO: 5
CGPKDTPEGAELKPWYC

SEQ ID NO: 6
CGQKETPEGAEAKPWYC

SEQ ID NO: 7
CGQRETPEGAEARPWYC

SEQ ID NO: 8
CGQRETPEGAEAKPC

SEQ ID NO: 9
CQRETPEGAEAKPWYC

SEQ ID NO: 10
CGQRETPEGAEAKFWYC

SEQ ID NO: 11
KSPGQRETPEGAEAKPWYE

SEQ ID NO: 12
KGQRETPEGAEAKPWYG

SEQ ID NO: 13
Ornithine-GQRETPEGAEAKPWYG

SEQ ID NO: 14
4-aminobutanoic acid-GQRETPEGAEAKPWYD

SEQ ID NO: 15
β-alanine-GQRETPEGAEAKPWYE

SEQ ID NO: 16
TKPIELGPDEPKAV

SEQ ID NO: 17
CGTKPIELGPDEPKAVC

SEQ ID NO: 18
GQRETPEGAEAKPWY

SEQ ID NO: 19
CGQREAPAGAAAKPWYC

SEQ ID NO: 20
TXEXXE

SEQ ID NO: 21
X$_1$-GQRETPEGAEAKPWY-X$_2$
```

The invention claimed is:

1. A method for therapeutic treatment of the pulmonary form of altitude sickness, comprising
administering to a patient having the pulmonary form of altitude sickness an effective amount of a peptide,
wherein the peptide is 17-20 amino acids in length and comprises the amino acid sequence CGQREFPEGAEAKPWYC (SEQ ID NO: 1),
wherein the peptide does not have tumor necrosis factor receptor binding activity,
wherein the peptide is cyclized, and
wherein the peptide is formulated in a nebulizble powder formulation.

2. The method according to claim 1, wherein the peptide is cyclized via the C residues.

3. The method according to claim 2, wherein the peptide is cyclized by a disulphide bridge between the C residues.

4. The method according to claim 1, wherein the nebulizable powder formulation further comprises a pharmaceutically acceptable carrier.

5. The method according to claim 4, wherein the peptide is administered to the patient in a quantity of 1 μg to 10 g.

6. The method according to claim 5, wherein the peptide is administered to the patient in a quantity of 10 μg to 1 g.

7. The method according to claim 5, wherein the peptide is administered to the patient in a quantity of 1 mg to 100 mg.

8. The method of claim 1, further comprising the step of obtaining an emergency pack for a mountaineer prior to said administering, the emergency pack comprising the effective amount of the peptide and a powder inhaler for said administering.

9. A method for therapeutic treatment of the pulmonary form of altitude sickness, comprising
administering by inhalation an effective amount of a peptide to a patient having the pulmonary firm of altitude sickness, wherein the pulmonary form of altitude sickness is treated by said administering,
wherein the peptide consists of the amino acid sequence CGQRETPEGAEAKPWYC (SEQ ID NO: 1) and is cyclized via the C residues, and
wherein the peptide is formulated as a powder for inhalation.

10. The method of claim 9, further comprising the step of obtaining an emergency pack for a mountaineer prior to said administering, the emergency pack comprising the effective amount of the peptide and a powder inhaler for said administering.

* * * * *

SEQUENCE LISTING

```
<160> NUMBER OF SEQ IDS NOS: 20

<210> SEQ ID NO 1
<211> LENGTH: 17
<212> TYPE: PRT
<213> ORGANISM: Artificial Sequence
<220> FEATURE:
<223> OTHER INFORMATION: Synthetic peptide

<400> SEQUENCE: 1

Cys Gly Gln Arg Glu Thr Pro Glu Gly Ala Glu Ala Lys Pro Trp Tyr
1               5                   10                  15

Cys

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Thr Pro Glu Gly Ala Glu
1               5
```

```
<210> SEQ ID NO 3
<211> LENGTH: 14
<212> TYPE: PRT
<213> ORGANISM: Artificial Sequence
<220> FEATURE:
<223> OTHER INFORMATION: Synthetic peptide

<400> SEQUENCE: 3

Gln Arg Glu Thr Pro Glu Gly Ala Glu Ala Lys Pro Trp Tyr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic peptide

<400> SEQUENCE: 4

Pro Lys Asp Thr Pro Glu Gly Ala Glu Leu Lys Pro Trp Tyr
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Synthetic peptide

<400> SEQUENCE: 5

Cys Gly Pro Lys Asp Thr Pro Glu Gly Ala Glu Leu Lys Pro Trp Tyr
1               5                   10                  15

Cys

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide

<400> SEQUENCE: 6

Cys Gly Gln Lys Glu Thr Pro Glu Gly Ala Glu Ala Lys Pro Trp Tyr
1               5                   10                  15

Cys

<210> SEQ ID NO 7
<211> LENGTH: 17
<212> TYPE: PRT
<213> ORGANISM: Artificial Sequence
<220> FEATURE:
<223> OTHER INFORMATION: Synthetic peptide

<400> SEQUENCE: 7

Cys Gly Gln Arg Glu Thr Pro Glu Gly Ala Glu Ala Arg Pro Trp Tyr
1               5                   10                  15

Cys

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide
```

```
<400> SEQUENCE: 8

Cys Gly Gln Arg Glu Thr Pro Glu Gly Ala Glu Ala Lys Pro Cys
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic peptide

<400> SEQUENCE: 9

Cys Gln Arg Glu Thr Pro Glu Gly Ala Glu Ala Lys Pro Trp Tyr Cys
1               5                   10                  15

<210> SEQ ID NO 10
<211> LENGTH: 17
<212> TYPE: PRT
<213> ORGANISM: Artificial Sequence
<220> FEATURE:
<223> OTHER INFORMATION: Synthetic peptide

<400> SEQUENCE: 10

Cys Gly Gln Arg Glu Thr Pro Glu Gly Ala Glu Ala Lys Phe Trp Tyr
1               5                   10                  15

Cys

<210> SEQ ID NO 11
<211> LENGTH: 19
<212> TYPE: PRT
<213> ORGANISM: Artificial Sequence
<220> FEATURE:
<223> OTHER INFORMATION: Synthetic peptide

<400> SEQUENCE: 11

Lys Ser Pro Gly Gln Arg Glu Thr Pro Glu Gly Ala Glu Ala Lys Pro
1               5                   10                  15

Trp Tyr Glu

<210> SEQ ID NO 12
<211> LENGTH: 17
<212> TYPE: PRT
<213> ORGANISM: Artificial Sequence
<220> FEATURE:
<223> OTHER INFORMATION: Synthetic peptide

<400> SEQUENCE: 12

Lys Gly Gln Arg Glu Thr Pro Glu Gly Ala Glu Ala Lys Pro Trp Tyr
1               5                   10                  15

Gly

<210> SEQ ID NO 13
<211> LENGTH: 16
<212> TYPE: PRT
<213> ORGANISM: Artificial Sequence
<220> FEATURE:
<223> OTHER INFORMATION: Synthetic peptide

<400> SEQUENCE: 13

Gly Gln Arg Glu Thr Pro Glu Gly Ala Glu Ala Lys Pro Trp Tyr Gly
1               5                   10                  15
```

```
<210> SEQ ID NO 14
<211> LENGTH: 16
<212> TYPE: PRT
<213> ORGANISM: Artificial Sequence
<220> FEATURE:
<223> OTHER INFORMATION: Synthetic peptide

<400> SEQUENCE: 14

Gly Gln Arg Glu Thr Pro Glu Gly Ala Glu Ala Lys Pro Trp Tyr Asp
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic peptide

<400> SEQUENCE: 15

Gly Gln Arg Glu Thr Pro Glu Gly Ala Glu Ala Lys Pro Trp Tyr Glu
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: Synthetic peptide

<400> SEQUENCE: 16

Thr Lys Pro Ile Glu Leu Gly Pro Asp Glu Pro Lys Ala Val
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Synthetic peptide

<400> SEQUENCE: 17

Cys Gly Thr Lys Pro Ile Glu Leu Gly Pro Asp Glu Pro Lys Ala Val
1               5                   10                  15

Cys

<210> SEQ ID NO 18
<211> LENGTH: 15
<212> TYPE: PRT
<213> ORGANISM: Artificial Sequence
<220> FEATURE:
<223> OTHER INFORMATION: Synthetic peptide

<400> SEQUENCE: 18

Gly Gln Arg Glu Thr Pro Glu Gly Ala Glu Ala Lys Pro Trp Tyr
1               5                   10                  15

<210> SEQ ID NO 19
<211> LENGTH: 17
<212> TYPE: PRT
<213> ORGANISM: Artificial Sequence
<220> FEATURE:
<223> OTHER INFORMATION: Synthetic peptide
```

```
-continued

<400> SEQUENCE: 19

Cys Gly Gln Arg Glu Ala Pro Ala Gly Ala Ala Ala Lys Pro Trp Tyr
1               5                   10                  15
Cys

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 20

Thr Xaa Glu Xaa Xaa Glu
1               5
```